(12) United States Patent
Jin et al.

(10) Patent No.: US 8,455,218 B2
(45) Date of Patent: Jun. 4, 2013

(54) **METHODS FOR G-CSF PRODUCTION IN A *PSEUDOMONAS* HOST CELL**

(75) Inventors: Hongfan Jin, San Diego, CA (US); Lawrence Chew, San Diego, CA (US)

(73) Assignee: Pfenex, Inc., San Diego, CA (US)

( * ) Notice: Subject to any disclaimer, the term of this patent is extended or adjusted under 35 U.S.C. 154(b) by 0 days.

(21) Appl. No.: 13/076,315

(22) Filed: Mar. 30, 2011

(65) Prior Publication Data

US 2011/0245474 A1 Oct. 6, 2011

Related U.S. Application Data

(60) Provisional application No. 61/320,239, filed on Apr. 1, 2010.

(51) Int. Cl.
*C12N 15/09* (2006.01)
*C12N 15/10* (2006.01)
*C12P 21/06* (2006.01)

(52) U.S. Cl.
USPC .................. 435/69.1; 435/69.5; 435/71.2

(58) Field of Classification Search
None
See application file for complete search history.

(56) References Cited

U.S. PATENT DOCUMENTS

| | | | |
|---|---|---|---|
| 4,551,433 A | 11/1985 | DeBoer | |
| 4,695,455 A | 9/1987 | Barnes et al. | |
| 4,755,465 A | 7/1988 | Gray et al. | |
| 4,810,643 A | 3/1989 | Souza | |
| 4,861,595 A | 8/1989 | Barnes et al. | |
| 4,904,584 A | 2/1990 | Shaw | |
| 5,055,294 A | 10/1991 | Gilroy | |
| 5,128,130 A | 7/1992 | Gilroy et al. | |
| 5,169,760 A | 12/1992 | Wilcox | |
| 5,281,532 A | 1/1994 | Rammler et al. | |
| 5,508,192 A | 4/1996 | Georgiou et al. | |
| 5,824,778 A | 10/1998 | Ishikawa et al. | |
| 5,824,784 A | 10/1998 | Kinstler et al. | |
| 7,001,892 B1 * | 2/2006 | Chmielewski et al. | 514/53 |
| 7,070,989 B2 | 7/2006 | Lee et al. | |
| 7,618,799 B2 * | 11/2009 | Coleman et al. | 435/183 |
| 2003/0167531 A1 * | 9/2003 | Russell et al. | 800/288 |
| 2005/0283000 A1 | 12/2005 | Menart et al. | |
| 2006/0008877 A1 | 1/2006 | Retallack et al. | |
| 2006/0040352 A1 | 2/2006 | Retallack et al. | |
| 2006/0110747 A1 | 5/2006 | Ramseier et al. | |
| 2007/0292918 A1 | 12/2007 | Stelman et al. | |
| 2008/0193974 A1 * | 8/2008 | Coleman et al. | 435/69.1 |
| 2008/0269070 A1 * | 10/2008 | Ramseier et al. | 506/14 |
| 2009/0092582 A1 | 4/2009 | Bogin et al. | |
| 2009/0275518 A1 | 11/2009 | Gonthier et al. | |
| 2009/0325230 A1 | 12/2009 | Schneider et al. | |
| 2010/0137162 A1 | 6/2010 | Retallack et al. | |

FOREIGN PATENT DOCUMENTS

| | | |
|---|---|---|
| AU | 76380/91 | 11/1991 |
| AU | 10948/92 | 8/1992 |
| EP | 0207459 | 1/1987 |
| EP | 0243153 | 10/1987 |
| EP | 0272703 | 12/1987 |
| EP | 0331186 | 9/1989 |
| EP | 0335423 | 10/1989 |
| EP | 0401384 | 12/1990 |
| EP | 0459630 | 12/1991 |
| EP | 0473268 | 3/1992 |
| WO | WO 90/12874 | 11/1990 |
| WO | WO 92/06116 | 4/1992 |
| WO | WO 95/13393 | 5/1995 |
| WO | WO 95/21254 | 8/1995 |
| WO | WO 95/33057 | 12/1995 |
| WO | WO 96/39422 | 12/1996 |
| WO | WO 99/58662 | 11/1999 |
| WO | WO 01/73081 | 10/2001 |
| WO | WO 02/20766 | 3/2002 |
| WO | WO 02/20767 | 3/2002 |
| WO | WO 02/066514 | 8/2002 |
| WO | WO 02/069232 | 9/2002 |
| WO | WO 02/077034 | 10/2002 |
| WO | WO 03/006501 | 1/2003 |
| WO | WO 03/027288 | 4/2003 |
| WO | WO 03/031464 | 4/2003 |
| WO | WO 03/076567 | 9/2003 |
| WO | WO 2004/020576 | 3/2004 |
| WO | WO-2007-107882 | 9/2007 |

OTHER PUBLICATIONS

Squires et al., Bioprocess International, 2004, 54-56, 58-59.*
Bergey's Manual of Determinative Bacteriology, R.E. Buchanan and N. E. Gibbons eds., pp. 217-289, 8$^{th}$ ed., The Williams & Wilkins Co., Baltimore, MD, 1974.
Choi et al., "Development and optimization of two-stage cyclic fed-batch culture for hG-CSF production using L-arabinose promoter of *Escherichia coli*," Bioprocess and Biosystems Engineering 24 (2001) 51-58.
Choi et al., "Plasmid Stability in Long-Term hG-CSF Production Using L-Arabinose Promoter System of *Escherichia coli*," J. Microbiol. Biotechnol. (2000) 10(3), 321-326.
Chung et al., "Overproduction of Human Granulocyte-Cology Stimulating Factor Fused to the PelB Signal Peptide in *Escherichia coli*," Journ. of Fermentation and Bioengineering, vol. 85, No. 4, 443-446 (1998).
Cusi M. Grazia and D. Ferrero, Harlequin granulocyte-colony stimulating factor interleukin 6 molecules with bifunctional and antagonistic activities, Immunotechnology JID-9511979 3 (1):61-69, 1997.
Davis and Mingioli, "Mutants of *Escherichia coli* requiring methionine or Vitamin B12," Bact 60:17-28 (1950).

(Continued)

*Primary Examiner* — Gyan Chandra
(74) *Attorney, Agent, or Firm* — Wilson, Sonsini, Goodrich & Rosati

(57) ABSTRACT

The present invention relates to the field of recombinant protein production in bacterial hosts. It further relates to expression of soluble, active recombinant protein by using secretion signals to direct the protein to the periplasmic space of a bacterial cell. In particular, the present invention relates to a production process for obtaining soluble hG-CSF protein from a bacterial host.

26 Claims, 8 Drawing Sheets

OTHER PUBLICATIONS

Devlin et al., "Alteration of amino-terminal codons of human granulocyte-colony-stimulating factor increases expression levels and allows efficient processing by methionine aminopeptidase in *Escherichia coli*," Gene, 65 (1988) 13-22.

Frishman et al., "Starts of Bacterial Genes: Estimating the Reliability of Computer Predictions," Gene 234(20):257-265 (1999).

Ghane, et al., "Over Expression of Biologically Active Interferon Beta Using Synthetic Gene in *E. coli*," Journ. of Sciences, Islamic Republic of Iran 19(3): 203-209 (2008).

Hong et al., "Production of biologically active hG-CSF by transgenic plant cell suspension culture," Enzyme and Microbial Technology 30 (2002) 763-767.

Ikehata et al., "Primary structure of nitrile hydratase deduced from the nucleotide sequence of a *Rhodococcus* species and its expression in *Escherichia coli*," Eur J Biochem 181(3):563-570 (1989).

Krishna R. et al., (2008) Mol Biotechnology "Optimization of the AT-content of Codons Immediately Downstream of the Initiation Codon and Evaluation of Culture Conditions for High-level Expression of Recombinant Human G-CSF in *Escherichia coli*," 38:221-232.

Jeong et al., "Secretory Production of Human Granulocyte Colony-Stimulating Factor in *Escherichia coli*," Protein Expression and Purification 23, 311-318 (2001).

Jevsevar et al., "Production of Nonclassical Inclusion Bodies from Which Correctly Folded Protein Can Be Extracted," Biotechnol. P. (2005) 21, 632-639.

Kang et al., "High Level Expression and Simple Purification of Recombinant Human Granulocyte Colony-Stimulating Factor in *E. coli*," Biotechnology Letters, vol. 17, No. 7 (1995) 687-692.

Neupogen (Filgrastim) Prescription Drug Product Insert (Sep. 2007).

Perez-Perez et al., "DNAK/DNAJ Supplementation Improves the Periplasmic Production of Human Granulocyte-Colony Stimulating Factor in *Escherichia coli*," Biochemical and Biophysical Research Communications, vol. 210, No. 2, 1995, pp. 524-529.

Rao et al., "Optimization of the AT-content of Codons Immediately Downstream of the Initiation Codon and Evaluation of Culture Conditions for High-level Epression of Recombinant Human G-CSF in *Escherichia coli*," Mol. Biotechnol (2008) 38:221-232.

Riesenberg, D et al., 1991, "High cell density cultivation of *Escherichia coli* at controlled specific growth rate," J. Biotechnol. 20 (1):17-27.

J. Sanchez-Romero & V. De Lorenzo (1999) Manual of Industrial Microbiology and Biotechnology (A. Demain & J. Davies, eds.) pp. 460-74 (ASM Press, Washington, D.C.).

Schneider, et al., 2005, "Auxotrophic markers pyrF and proC can replace antibiotic markers on protein production plasmids in high-cell-density *Pseudomonas fluorescens* fermentation," Biotechnol. Progress 21(2): 343-8.

Schweizer, "Vectors to express foreign genes and techniques to monitor gene expression in *Pseudomondas*," Curr Op Biotech 12:439-445 (2001).

R. Slater & R. Williams, Molecular Biology and Biotechnology, J. Walker & R. Rapley, eds., pp. 125-154 , The Royal Society of Chemistry, Cambridge, UK, 2000.

R. Sorg, J. Enczmann, U. Sorg, K. Heermeier, E. M. Schneider, and P. Wernet. Rapid and sensitive mRNA phenotyping for interleukins (IL-1 to IL-6) and colony-stimulating factors (G-CSF, M-CSF, and GM-CSF) by reverse transcription and subsequent polymerase chain reaction, Exp Hematol JID-0402313 19 (9):882-887, 1991.

B. E. Suzek et al., "A probabilistic method for identifying start codons in bacterial genomes," Bioinformatics 17(12):1123-30 (Dec. 2001).

Vanz et al., "Human Granulocyte Colony Stimulating factor (hG-CSF): cloning, overexpression, purification and characterization," Microbial Cell Factories 2008, 7:13.

Welch, et al., 2009, PLoS One, "Design Parameters to Control Synthetic Gene Expression in *Escherichia coli*," 4(9): e7002.

Weston, B., Todd, R. F., 3rd, Axtell, R., Balazovich, K., Stewart, J., Locey, B. J., Mayo-Bond, L., Loos, P., Hutchinson, R. & Boxer, L. A. (1991). Severe congenital neutropenia: clinical effects and neutrophil function during treatment with granulocyte colony-stimulating factor. *J Lab Clin Med* 117, 282-90.

Wingfield et al., Characterization of recombinant-derived granulocyte-colony stimulating factor (G-CSF), Biochem. J. (1988) 256, 213-218.

Zaveckas et al., "Effect of Surface histidine mutations and their number on the partitioning and refolding of recombinant human granulocyte-colony stimulating factor (Cys17Ser) in aqueous two-phase systems containing chelated metal ions," Journ. of Chromatography B, 852 (2007) 409-419.

Yoon et al., "Secretory Production of Recombinant Proteins in *Escherichia coli*, " Recent Patents on Biotechnology, 4, 23-29 (2010).

PCT/US2011/030593 International Search Report dated Dec. 23, 2011.

Botos et al., "The Catalytic Domain of *Escherichia coli* Lon Protease Has a Unique Fold and a Ser-Lys Dyad in the Active Site," 2004, The Journal of Biological Chemistry, vol. 279, No. 9: 8140-8148.

Covalt J.C.et al., "Temperature, media, and point of induction affect the N-terminal processing of interleukin-1beta," Protein Expr Purif 41: 45-52 (2005).

Gilbert et al., "A New Cell Surface Proteinase: Sequencing and Analysis of the *prtB* Gene from *Lactobacillus delbrueckii* subsp. *Bulgaricus*," Journal of Bacteriology, 1996, 178(11): 3059-3065.

Hammerling et al., "In Vitro bioassay with enhanced sensitivity for human granulocyte colony-stimulating factor." J. Pharm. Biomed. Anal. 3 (1995) 9-20.

Herman et al., "Characterization, formulation and stability of Neupogen (Filgrastim), a recombinant human granulocyte-colony stimulation factor." Pharmaceutical Biotechnology, edited by Pearlman and Wang, vol. 9, (1996) 303-28.

Jin et al., "Soluble periplasmic production of human granulocyte colony-stimulating factor (G-CSF) in *Pseudomonas fluorescens*," Protein Expression and Purification, vol. 78(1), (2011): 69-77.

Keiler, K.C. & Sauer, R.T., "Identification of Active site Residues of the Tsp Protease," The Journal of Biological Chemistry, 1995, vol. 270, No. 48, pp. 28864-28868.

Kramer, Irene, Ph.D., "Recombinant G-CSF products and what pharmacists need to know," European Journal of Hospital Pharmacists, May 2011, vol. 17, pp. 36-45.

Louis et al., "Specificity of *Pseudomonas aeruginosa* serralysin revisited using biologically active peptides as substrates," Biochimica et Biophysica Acta, 1998, pp. 378-386.

Okabe, et al., "In vitro and in vivo hematopoietic effect of mutant human granulocyte colony-stimulating factor," Blood, 75, (1990), pp. 1788-1793.

Pallen, M.J. & Wren, B.W., "The HtrA Family of serine proteases," Molecular Microbiology, 1997, 26(2), pp. 209-221.

Patterson-Ward et al., "Detection and characterization of two ATP-dependent conformational changes in proteolytically inactive *Escherichia coli* Lon mutants by stopped flow kinetic techniques," Biochemistry, 2007, 46(47): 13593-13605 doi:10.1021/bi701649b.

Retallack et al., "Transport of heterologous proteins to the periplasmic space of *Pseudomonas fluorescens* using a variety of native signal sequences," Biotechnol Lett 29, (2007), pp. 1483-1491.

Sakoh et al., "Proteolytic Activity of HtpX, a Membrane-bound and Stress-controlled Protease from *Escherichia coli*," 2005, Journal of Biological Chemistry, vol. 280, No. 39, pp. 33305-33310.

Tanaka et al., "Three types of recombinant human granulocyte colony-stimulating factor have equivalent biological activities in monkeys," Cytokine 9, (1997), pp. 360-369.

* cited by examiner

GCSF DNA Sequence

```
  1  Met Thr Pro Leu Gly Pro Ala Ser Ser Leu Pro Gln Ser Phe Leu Leu Lys Cys Leu Glu
     ATG ACT CCT CTG GGT CCT GCA AGT AGT CTG CCG CAA AGT TTT CTC CTG AAG TGC CTG GAA

61  Gln Val Arg Lys Ile Gln Gly Asp Gly Ala Ala Leu Gln Glu Lys Leu Cys Ala Thr Tyr
     CAG GTG CGC AAA ATT CAG GGC GAC GGC GCA GCA CTG CAG GAA AAA CTG TGC GCG ACC TAT

121  Lys Leu Cys His Pro Glu Glu Leu Val Leu Leu Gly His Ser Leu Gly Ile Pro Trp Ala
     AAG TTG TGC CAC CCC GAA GAA CTG GTG CTG CTG GGC CAT AGC CTG GGG ATT CCA TGG GCG

181  Pro Leu Ser Ser Cys Pro Ser Gln Ala Leu Gln Leu Ala Gly Cys Leu Ser Gln Leu His
     CCG CTG TCG TCC TGT CCT AGT CAA GCC TTG CAA TTG GCC GGT TGC CTC TCG CAA CTG CAT

241  Ser Gly Leu Phe Leu Tyr Gln Gly Leu Leu Gln Ala Leu Glu Gly Ile Ser Pro Glu Leu
     AGC GGC CTG TTC CTG TAC CAA GGC CTG CTG CAG GCC TTG GAA GGT ATC TCC CCG GAA CTG

301  Gly Pro Thr Leu Asp Thr Leu Gln Leu Asp Val Ala Asp Phe Ala Thr Thr Ile Trp Gln
     GGC CCG ACG CTG GAT ACC CTG CAA CTG GAC GTA GCA GAT TTC GCC ACG ATC TGG CAG

361  Gln Met Glu Glu Leu Gly Met Ala Pro Ala Leu Gln Pro Thr Gln Gly Ala Met Pro Ala
     CAG ATG GAA GAA CTG GGC ATG GCC CCG GCC CTC CAG CCC ACG CAA GGC GCG ATG CCT GCA

421  Phe Ala Ser Ala Phe Gln Arg Arg Ala Gly Gly Val Leu Val Ala Ser His Leu Gln Ser
     TTC GCC TCG GCG TTT CAA CGT CGT GCG GGT GGC GTG CTG GTA GCC AGC CAT TTG CAG AGC

481  Phe Leu Glu Val Ser Tyr Arg Val Leu Arg His Leu Ala Gln Pro
     TTT CTG GAG GTG AGC TAT CGC GTC CTC CAT CTC GCC CAA CCG
```

FIGURE 6

```
GCSF Amino Acid Sequence

1  Met Thr Pro Leu Gly Pro Ala Ser Ser Leu Pro Gln Ser Phe Leu Leu Lys Cys Leu Glu
 21  Gln Val Arg Lys Ile Gln Gly Asp Gly Ala Ala Leu Gln Glu Lys Leu Cys Ala Thr Tyr
 41  Lys Leu Cys His Pro Glu Glu Leu Val Leu Leu Gly His Ser Leu Gly Ile Pro Trp Ala
 61  Pro Leu Ser Ser Cys Pro Ser Gln Ala Leu Gln Leu Ala Gly Cys Leu Ser Gln Leu His
 81  Ser Gly Leu Phe Leu Tyr Gln Gly Leu Leu Gln Ala Leu Glu Gly Ile Ser Pro Glu Leu
101  Gly Pro Thr Leu Asp Thr Leu Gln Leu Asp Val Ala Asp Phe Ala Thr Thr Ile Trp Gln
121  Gln Met Glu Glu Leu Gly Met Ala Pro Ala Leu Gln Pro Thr Gln Gly Ala Met Pro Ala
141  Phe Ala Ser Ala Phe Gln Arg Arg Ala Gly Gly Val Leu Val Ala Ser His Leu Gln Ser
161  Phe Leu Glu Val Ser Tyr Arg Val Leu Arg His Leu Ala Gln Pro
```

METHODS FOR G-CSF PRODUCTION IN A *PSEUDOMONAS* HOST CELL

CLAIM OF PRIORITY

This application claims priority under 35 U.S.C. §119(e) to U.S. Provisional Application Ser. No. 61/320,239, filed Apr. 1, 2010. The content of this application is hereby incorporated by reference in its entirety.

SEQUENCE LISTING

The instant application contains a Sequence Listing which has been submitted via EFS-Web and is hereby incorporated by reference in its entirety. Said ASCII copy, created on Sep. 7, 2012, is named 38194201.txt and is 27,653 bytes in size.

BACKGROUND OF THE INVENTION

Human granulocyte colony-stimulating factor (hG-CSF) is a cytokine that can play a role in the proliferation and differentiation of hemopoietic precursor cells and the activation of mature neutrophilic granulocytes. Recombinant hG-CSF can be used, for example, as an injectable to i) selectively stimulate the growth of white blood cells, ii) to help reduce the incidence of infection in patients undergoing certain cancer chemotherapy, iii) for the mobilization of peripheral blood progenitor cells, and iv) for the treatment of severe chronic neutropenia.

Two forms of recombinant hG-CSF are currently available for clinical use on the market: a glycosylated form obtained by expression in mammalian cells and a non-glycosylated form synthesized in an *E. coli* expression system. Economical large-scale production of recombinant hG-CSF is still a great challenge with respect to biosynthesis and downstream processing because the expression efficiency of a hG-CSF gene in the *E. coli* expression system is low and overexpression generally results in partitioning of the expressed protein as insoluble material in inclusion bodies. Expression of hG-CSF in insoluble inclusion bodies (IBs) can require lengthy downstream process to solublize and refold the target protein. The available periplasmically expressed hG-CSF products either lack the N-terminal methionine or have alternative N-terminal sequence compared to the drug Filgrastim. There has been work reported in *E. coli* relating to secretion of hG-CSF in a soluble form; however, in these expression systems a peptide tag was added and tag removal upon purification required. Thus, there is a need for new methods of expressing hG-CSF comprising an N-terminal methionine (Met-G-CSF) and no sequence tag.

SUMMARY OF THE INVENTION

The present invention relates to the expression of recombinant human G-CSF protein fused to a secretion signal in a *Pseudomonad* host cell, wherein the recombinant human G-CSF protein can be directed to the periplasm of the *Pseudomonad* host cell, and soluble recombinant human G-CSF can be generated that lacks the secretion signal and comprises and N-terminal methionine (Met-G-CSF).

In particular, the present invention provides a method comprising producing a G-CSF protein in a *Pseudomonad* host cell, wherein the G-CSF comprises an N-terminal methionine, and wherein said *Pseudomonad* host cell comprises a mutation in a gene expressing a protease.

In embodiments, the producing comprises expressing said G-CSF protein from an expression construct. In certain embodiments, the expression construct is a plasmid. In other embodiments, the expression construct comprises sequence encoding G-CSF protein fused to a secretion signal. In certain embodiments, the secretion signal directs transfer of the G-CSF protein to the periplasm in the *Pseudomonas* host cell. In certain embodiments, the secretion signal is cleaved from said G-CSF protein in said *Pseudomonad* host cell. In certain embodiments, the secretion signal protein sequence comprises any one of SEQ ID NOs: 8-26. In certain embodiments, at least 50% of said G-CSF protein is expressed in the soluble fraction.

In embodiments, the protease is a serine protease. In embodiments, the serine protease is PrtB, and its gene is prtB. In other embodiments, the mutation is a complete deletion.

In embodiments, the *Pseudomonas* host cell is a *Pseudomonas* host cell. In certain embodiments, the *Pseudomonas* host cell is a *Pseudomonas fluorescens* host cell.

In embodiments, the G-CSF protein is human G-CSF protein. In embodiments, the yield of said G-CSF protein is about 0.1 g/L to 10 g/L. In embodiments, the G-CSF protein is active. In embodiments, the activity is determined by binding recombinant G-CSF receptor.

The invention further includes a method comprising producing a G-CSF protein in a *Pseudomonas* host cell, wherein the G-CSF comprises an N-terminal methionine, and the yield of Met-G-CSF protein is about 0.1 g/L to 10 g/L. In embodiments, the method comprises expressing said G-CSF protein from an expression construct. In other embodiments, said expression construct is a plasmid. In certain embodiments, the expression construct comprises a sequence encoding the G-CSF protein fused to a secretion signal. In embodiments, the secretion signal directs transfer of the G-CSF protein to the periplasm in the *Pseudomonas* host cell. In certain embodiments, the secretion signal is cleaved from said G-CSF protein in said *Pseudomonas* host cell. In certain embodiments, the secretion signal protein sequence comprises any one of SEQ ID NOs: 8-26. In certain embodiments, at least 50% of said G-CSF protein is expressed in the soluble fraction.

In embodiments, the *Pseudomonas* host cell is a *Pseudomonas* host cell. In certain embodiments, the *Pseudomonas* host cell is a *Pseudomonas fluorescens* host cell.

In embodiments, the G-CSF protein is human G-CSF protein. In certain embodiments, the G-CSF protein is active. In other embodiments, the activity is determined by binding recombinant G-CSF receptor.

The present invention also provides a composition comprising G-CSF protein obtained according to the methods described herein. In embodiments, the G-CSF protein comprises an N-terminal methionine. In embodiments, the recombinant toxin protein is produced in a strain of *P. fluorescens* identified herein as producing a high yield of the soluble protein and/or a high yield of GCSF comprising the N-terminal methionine. In certain embodiments, the recombinant GCSF protein is produced in a strain of *P. fluorescens* described herein as producing the highest yield of desirable GCSF protein. In other embodiments, the recombinant protein is produced in a strain of *P. fluorescens* described herein as one used for fermentation production of the GCSF protein. In specific embodiments, the recombinant protein is produced in a strain of *P. fluorescens* having a rxf08627 deletion, and further wherein the G-CSF protein is expressed from an expression construct comprising the sequence encoding the G-CSF protein fused to a DsbA secretion signal.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 6 shows an exemplary DNA sequence encoding hGCSF that has been optimized for expression in *P. fluorescens* (SEQ ID NO: 27), and the corresponding amino acid sequence (SEQ ID NO: 28).

FIG. 7 shows the h-GCSF amino acid sequence (SEQ ID NO: 28).

DETAILED DESCRIPTION OF THE INVENTION

Overview

Figure 1:
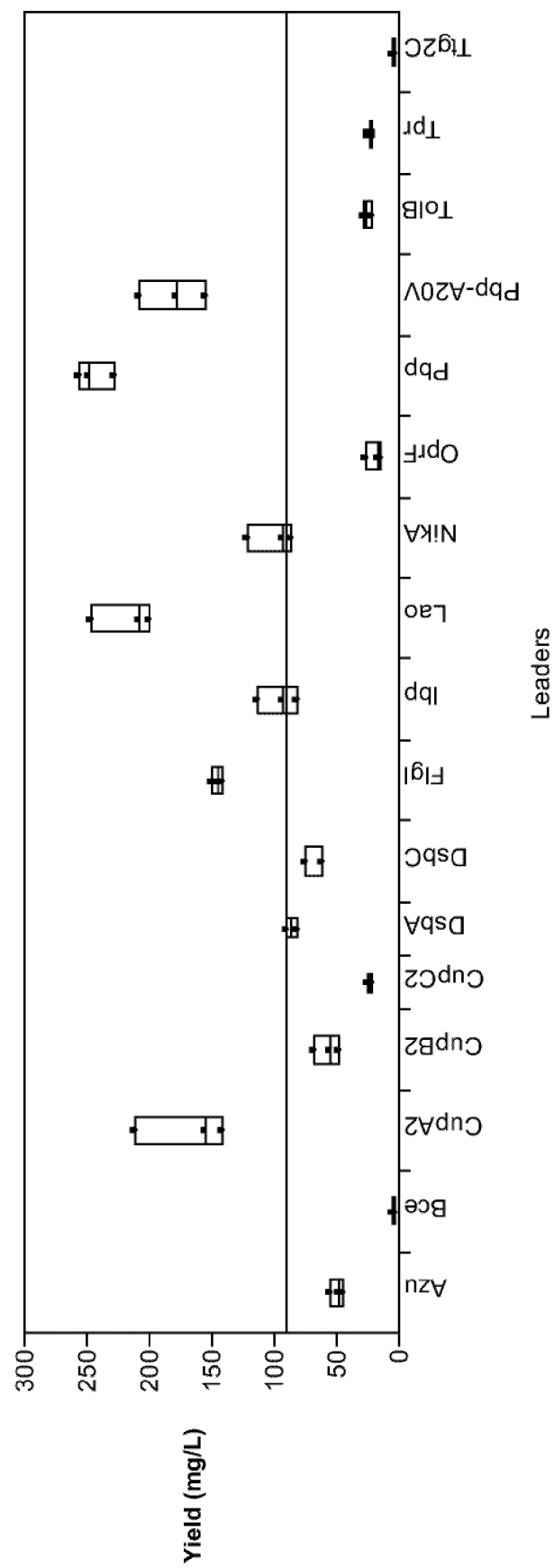
FIG. 1 illustrates expression analysis of the Met-G-CSF with 19 different secretion leaders. One-way analysis (quantiles) of soluble volumetric G-CSF expression, as quantified by BLI interferometry, using JMP Software (Cary, N.C.). Each bar represents results from a single expression strain, and yields for each of three replicates are represented by black dots. The expression level for all strains is shown. For convenience, the periplasmic Met-G-CSF constructs are represented by the secretion leaders.

The present invention relates to methods for producing soluble recombinant human granulocyte colony-stimulating factor (hG-CSF) in a *Pseudomonas* host cell. High levels of expression of recombinant hG-CSF can be achieved, and the hG-CSF protein can be prepared to a high level of purity. The host cell can be *Pseudomonas fluorescens*. The codons in a construct used to express hG-CSF can be selected to be optimized for expression of hG-CSF in the host strain used, e.g., *Pseudomonas fluorescens*.

Nucleic acid constructs can encode hG-CSF fused to any of a selection of native secretion leaders, e.g., secretion leaders native to *P. fluorescens*. Any of a variety genetic backgrounds of *Pseudomonas* stains, e.g., *P. fluorescens* host strains, can be used. In one embodiment, the genetic background comprises a mutation in one or more genes that encode proteases. In another embodiment, the protease is prtB.

In one embodiment, the secretion leader can transport soluble hG-CSF to the periplasm. In other embodiments, the purification of hG-CSF does not require solubilization and subsequent refolding. In other embodiments, at least a portion of hG-CSF is not expressed in inclusion bodies. In other embodiments, recombinant hG-CSF is expressed devoid of any peptide tag for purification and therefore does not require additional processing upon purification. In other embodiments, the secretion leader is efficiently processed from the solubly expressed hG-CSF and the protein contains an N-terminal methionine (Met-G-CSF), the same as the drug Filgrastim. In other embodiments, the expressed protein is non-glycosylated, as is hG-CSF produced in *E coli*. In other embodiments, an expression plasmid for periplasmic production of hG-CSF does not utilize any antibiotic resistance marker gene for selection and maintenance, thus eliminating complicated processes for subsequent removal of plasmid DNA required for production of biopharmaceuticals. In other embodiments, fermentation conditions are scalable for large-volume production. The methods of the provided invention can yield high levels of soluble, active hG-CSF protein with an N-terminal methionine (Met-G-CSF).

G-CSF

Granulocyte colony-stimulating factor (also known as G-CSF, GCSF, colony-stimulating factor 3, CSF3, or CSF3OS) is a colony-stimulating factor hormone. In humans, G-CSF can be produced by a number of different tissues. G-CSF can be secreted by monocytes, macrophages, neutrophils, stromal cells, fibroblasts, and endothelial cells. Synthesis of G-CSF can be induced by bacterial endotoxins, TNF, IL1, IL17, and GM-CSF (granulocyte-macrophage colony stimulating factor). Prostaglandin E2 can inhibit the synthesis of G-CSF.

G-CSF can serve as a growth factor or cytokine that can stimulate the bone marrow to produce granulocytes and stem cells and release them into the blood. G-CSF can also stimulate the survival, proliferation, differentiation, and function of neutrophil precursors and mature neutrophils. G-CSF can regulate these cells using Janus kinase (JAK)/signal transducer and activator of transcription (STAT) and Ras/mitogen-activated protein (MAP) kinase and phosphatidylinositol 3-kinase (PI3K)/protein kinase B (Akt) signal transduction pathways.

DNA

The human G-CSF gene maps to chromosome 17q21-q22 and is located in the vicinity of a translocation break point which can occur in acute promyelocytic leukemias. The human G-CSF gene contains 5 exons and 4 introns. G-CSF mRNA can be differentially spliced, leading to the production of two variant forms of the protein, one shortened by 3 amino acids. The mouse orthologue of CSF3 HUMAN is CSF3 MOUSE (Swissprot databank) and is found on mouse chromosome 11. The genomic organization of the mouse gene is similar to that of the human (5 exons and 4 introns).

Protein

In human cells, two different polypeptides of G-CSF of molecular weight 19,600 can be synthesized from the same gene by differential mRNA splicing (Nagata et al., 1986; Souza et al., 1986; Metcalf, 1985). The G-CSF gene can encode a protein of 207 amino acids containing a hydrophobic secretory signal sequence of 30 amino acids. Swissprot databank lists a 207 amino acid form of G-CSF (P09919-1) and a 204 amino acid form (the "isoform short", P09919-2). Mature forms of the two polypeptides differ by the presence (long form) or absence (short form) of 3 amino acids (177 and 174 amino acids, respectively). Both the long and short form can have G-CSF biological activity.

G-CSF contains 5 cysteine residues, four of which can form disulfide bonds (between amino acids 36 and 42 and between amino acids 64 and 74) (numbered with respect to the mature (lacking the signal peptide) short form of the polypeptide). A free cysteine can be found at position 17. An O-glycosylation site can occur at Thr-133 in G-CSF. The protein can be glycosylated with O-glycan consisting of Gal-GalNAc disaccharide, which can be modified with up to two sialic acid residues (which occurs in recombinantly expressed G-CSF from CHO cells). The sugar moiety of G-CSF is not required for full biological activity. The biologically active form is a monomer.

Human G-CSF has four stretches of helices: between residues 11 and 41 (helix A), 71 and 95 (helix B), 102 and 125 (helix C), and 145 and 170 (helix D). A left-handed four-helix bundle can be formed, with helices A and B aligned parallel to one another (up-up) and antiparallel to helices C and D (down-down). Part of the AB loop connecting helices A and B has an additional short fifth helix (E). G-CSF has a pI of 5.5.

Sequence variants of hG-CSF are described, for example, in U.S. Patent Application No. 2009/0275518, which is incorporated herein in its entirety. hG-CSF and related mutants or variant cDNAs and proteins have been disclosed in EP0243153. Splicing variants of G-CSF have been reported in R. Sorg, J. Enczmann, U. Sorg, K. Heermeier, E. M. Schneider, and P. Wernet. Rapid and sensitive mRNA phenotyping for interleukins (IL-1 to IL-6) and colony-stimulating factors (G-CSF, M-CSF, and GM-CSF) by reverse transcription and subsequent polymerase chain reaction, Exp Hematol JID-0402313 19 (9):882-887, 1991; Cusi M. Grazia and D. Ferrero, Harlequin granulocyte-colony stimulating factor interleukin 6 molecules with bifunctional and antagonistic activities, Immunotechnology JID-9511979 3 (1):61-69, 1997; and WO03027288A1. Analogs of human G-CSF have been generated by mutagenesis or by fusion with heterologous sequences (e.g., PCT Application Nos. WO 04/020576; WO 02/020767; WO 02/020766; WO 02/066514; WO 02/077034; WO 03/076567; WO 02/069232; WO 01/073081; WO 99/58662; WO 96/39422; WO 95/21254; WO 95/13393; WO 95/33057; WO 92/06116; WO 90/12874; EP272703; EP459630; EP243153; U.S. Pat. No. 4,904,584; U.S. Pat. No. 4,810,643; AU 76380/91; and AU 10948/92). Non-natural variants of human G-CSF have been generated to improve their activity by mutagenizing specific residues and linking non-peptide moieties such as PEG molecules (e.g., PCT Application Publication Nos. WO 03/031464 and WO 03/006501; EP401384, EP473268, EP335423, and U.S. Pat. Nos. 5,824,778 and 5,824,784), all incorporated herein by reference in their entirety. Antibodies against human G-CSF have been described (e.g., EP0331186).

Recombinant G-CSF

Recombinant G-CSF is marketed under the generic names Filgrastim and Lenograstim and under the brand names Neupogen, Neutrogin, and Granocyte. Filgrastim is the generic name for a non-glycosylated recombinant G-CSF (brand name Neupogen; Amgen Inc., Thousand Oaks, Calif.). Filgrastim is a 175-amino acid protein produced by a gene encoding hG-CSF in *E. coli*. Filgrastim has an N-terminal methionine. Filgrastim also differs from the form of hG-CSF expressed in a human cell because Filgrastim lacks glycosylation. Lenograstim (brand name Graslopin, Granocyte), developed by Ligand Pharmaceuticals, is a glycosylated recombinant form of human granulocyte colony stimulating factor. Neulasta (pegfilgrastim) is obtained by attaching a 20 kDa monomethoxypolyethylene glycol to the N-terminal methionyl residue of Filgrastim (pegylated Filgrastim).

Filgrastim can be administered to patients receiving myelosuppressive chemotherapy, patients with acute myeloid leukemia that receive induction or consolidation chemotherapy, patients receiving bone marrow transplant, patients undergoing peripheral blood progenitor cell collection and therapy, or patients with severe chronic neutropenia.

A recombinant mutated form of human G-CSF is KW-2228 (Marograstim and Nartograstim), an N-terminally modified form of human G-CSF in which Thr1, Leu3, Gly4, Pro5, and Cys17 are substituted with Ala, Thr, Tyr, Arg, and Ser, respectively. This protein can be produced in *Escherichia coli*.

Modifications

In some embodiments, modified versions of hG-CSF can be generated. In general, with respect to an amino acid sequence, the term "modification" includes substitutions, insertions, elongations, deletions, and derivatizations alone or in combination. In some embodiments, the peptides may include one or more modifications of a "non-essential" amino acid residue. In this context, a "non-essential" amino acid residue is a residue that can be altered, e.g., deleted or substituted, in the novel amino acid sequence without abolishing or substantially reducing the activity (e.g., the agonist activity) of the peptide (e.g., the analog peptide). In some embodiments, the peptides may include one or more modifications of an "essential" amino acid residue. In this context, an "essential" amino acid residue is a residue that when altered, e.g., deleted or substituted, in the novel amino acid sequence the activity of the reference peptide is substantially reduced or abolished. In such embodiments where an essential amino acid residue is altered, the modified peptide may possess an activity of hG-CSF of interest in the methods provided. The substitutions, insertions and deletions may be at the N-terminal or C-terminal end, or may be at internal portions of the protein. By way of example, the protein may include 1, 2, 3, 4, 5, 6, 7, 8, 9, 10, or more substitutions, both in a consecutive manner or spaced throughout the peptide molecule. Alone or in combination with the substitutions, the peptide may include 1, 2, 3, 4, 5, 6, 7, 8, 9, 10, or more insertions, again either in consecutive manner or spaced throughout the peptide molecule. The peptide, alone or in combination with the substitutions and/or insertions, may also include 1, 2, 3, 4, 5, 6, 7, 8, 9, 10, or more deletions, again either in consecutive manner or spaced throughout the peptide molecule. The peptide, alone or in combination with the substitutions, insertions and/or deletions, may also include 1, 2, 3, 4, 5, 6, 7, 8, 9, 10, or more amino acid additions.

Substitutions include conservative amino acid substitutions. A "conservative amino acid substitution" is one in which the amino acid residue is replaced with an amino acid residue having a similar side chain, or physicochemical characteristics (e.g., electrostatic, hydrogen bonding, isosteric, hydrophobic features). The amino acids may be naturally occurring or normatural (unnatural). Families of amino acid residues having similar side chains are known in the art. These families include amino acids with basic side chains (e.g. lysine, arginine, histidine), acidic side chains (e.g., aspartic acid, glutamic acid), uncharged polar side chains (e.g., glycine, asparagine, glutamine, serine, threonine, tyrosine, methionine, cysteine), nonpolar side chains (e.g., alanine, valine, leucine, isoleucine, proline, phenylalanine, tryptophan), β-branched side chains (e.g., threonine, valine, isoleucine) and aromatic side chains (e.g., tyrosine, phenylalanine, tryptophan, histidine). Substitutions may also include non-conservative changes.

G-CSF Receptors

The G-CSF receptor (also known as CSF3R, CD114, or GCSFR) is expressed on all cells of the neutrophil and granulocyte lineage. It is expressed also in placenta cells, endothelial cells and various carcinoma cell lines. The human receptor has a length of 813 amino acids. CSF3R contains an extracellular ligand-binding domain, a transmembrane domain, and a cytoplasmic domain. The human receptor shows 62.5% sequence homology to the murine receptor. The receptor can bind G-CSF with high affinity ($K_{dis}$=550 picoM). The gene encoding the human G-CSF receptor (CSF3R) maps to chromosome 1p32-p34. 3.

At least four different forms of the human G-CSF receptor, resulting from alternative splicing of the mRNA, have been cloned. Three of the isoforms can be membrane-bound and the other can be secreted and soluble. One variant contains a deletion of the transmembrane region and is probably a soluble form of the receptor. Another variant contains 27 additional amino acids in its cytoplasmic domain.

Mutations in CSF3R are a cause of Kostmann syndrome, also known as severe congenital neutropenia. Severe congenital neutropenia (Kostmann syndrome) is characterized by profound absolute neutropenia and a maturation arrest of marrow progenitor cells at the stage of promyelocytes and myelocytes. A somatic point mutation in one allele of the G-CSF receptor gene in a patient with severe congenital neutropenia results in a cytoplasmic truncation of the receptor. The mutant receptor chain can transduce a strong growth signal but this signal is unable to trigger maturation. The mutant receptor chain may act in a dominant negative manner to block granulocytic maturation.

G-CSF can form a tetrameric complex with GCSFR. The complex can contain two ligand molecules and two receptor molecules. The N-terminal region (residues 20-46) and the carboxy terminal region (including helix D) of G-CSF can be involved in binding to the receptor. One receptor-binding site involves various residues on the helices A and C. A second binding site may be located on the helix E (1997, PMID 9194183; 2003, PMID 12946100). A residue that plays a role in receptor binding is Glu 19 (in helix A). Other residues that can play functional roles are Lys 40, Glu 46 (helix E) and Phe 144 (helix D). Val 48, Leu 49 (helix E), Leu 15 (helix A), Asp 112 and Leu 124 (helix C) appear to play a role in biological activity.

Expression Systems

The methods of the provided invention can comprise expressing recombinant hG-CSF from an expression construct in a *Pseudomonas* host cell. The expression construct can be, for example, a plasmid. In some embodiments, a plasmid encoding hG-CSF sequence can comprise a selection marker, and host cells maintaining the plasmid can be grown under selective conditions. In some embodiments, the plasmid does not comprise a selection marker. In some embodiments, the expression construct can be integrated into the host cell genome. In some embodiments, the expression construct encodes hG-CSF fused to a secretory signal that can direct hG-CSF to the periplasm. In some embodiments, the secetory signal can be cleaved in the host cell resulting in hG-CSF with an N-terminal methionine (Met-G-CSF).

Methods for expressing heterologous proteins, including useful regulatory sequences (e.g., promoters, secretion leaders, and ribosome binding sites), in *Pseudomonas* host cells, as well as host cells useful in the methods of the present invention, are described, e.g., in U.S. Pat. App. Pub. No. 2008/0269070 and U.S. patent application Ser. No. 12/610,207, both titled "Method for Rapidly Screening Microbial Hosts to Identify Certain Strains with Improved Yield and/or Quality in the Expression of Heterologous Proteins," U.S. Pat. App. Pub. No. 2006/0040352, "Expression of Mammalian Proteins in *Pseudomonas Fluorescens*," and U.S. Pat. App. Pub. No. 2006/0110747, "Process for Improved Protein Expression by Strain Engineering," all incorporated herein by reference in their entirety. These publications also describe bacterial host strains useful in practicing the methods of the invention, that have been engineered to overexpress folding modulators or wherein protease mutations have been introduced, in order to increase heterologous protein expression. Sequence leaders are described in detail in U.S. Patent App. Pub. No. 2008/0193974, "Bacterial leader sequences for increased expression," and U.S. Pat. App. Pub. No. 2006/0008877, "Expression systems with Sec-secretion," both incorporated herein by reference in their entirety, as well as in U.S. Pat. App. Ser. No. 12/610,207.

U.S. Pat. App. Pub. No. 2008/0269070, incorporated herein by reference, describes host cells having a mutation in a protease gene expressing a protease, resulting in the inactivation of the protease. Protease mutations described in U.S. Pat. App. Pub. No. 2008/0269070 include, for example, a mutation of a gene from which a serine peptidase, an S41 protease, an STE24 endopeptidase, or a lon protease is expressed. Inactivation of a protease by mutation in any of the protease open reading frames provided herein as SEQ ID NO: 29 (RXF01250, a serine peptidase), SEQ ID NO: 30 (RXF06586, an S41 protease), SEQ ID NO: 31 (RXF05137, htpX, an STE24 endopeptidase), SEQ ID NO: 32 (RXF04653, a lon protease), SEQ ID NO: 33 (RXF08627.2, PrtB, an extracellular serine protease), and SEQ ID NO: 34 (RXF04304.1, AprA, a serralysin) is contemplated.

Promoters

The promoters used in accordance with the present invention may be constitutive promoters or regulated promoters. Common examples of useful regulated promoters include those of the family derived from the lac promoter (i.e. the lacZ promoter), especially the tac and trc promoters described in U.S. Pat. No. 4,551,433 to DeBoer, as well as Ptac16, Ptac17, PtacII, PlacUV5, and the T7lac promoter. In one embodiment, the promoter is not derived from the host cell organism. In certain embodiments, the promoter is derived from an *E. coli* organism.

Inducible promoter sequences can be used to regulate expression of hG-CSF in accordance with the methods of the invention. In embodiments, inducible promoters useful in the methods of the present invention include those of the family derived from the lac promoter (i.e. the lacZ promoter), especially the tac and trc promoters described in U.S. Pat. No. 4,551,433 to DeBoer, as well as Ptac16, Ptac17, PtacII, PlacUV5, and the T7lac promoter. In one embodiment, the promoter is not derived from the host cell organism. In certain embodiments, the promoter is derived from an *E. coli* organism. In some embodiments, a lac promoter is used to regulate expression of hG-CSF from a plasmid. In the case of the lac promoter derivatives or family members, e.g., the tac promoter, an inducer is IPTG (isopropyl-β-D-1-thiogalactopyranoside, also called "isopropylthiogalactoside"). In certain embodiments, IPTG is added to culture to induce expression of hG-CSF from a lac promoter in a *Pseudomonas* host cell.

Common examples of non-lac-type promoters useful in expression systems according to the present invention include, e.g., those listed in Table 1.

TABLE 1

Examples of non-lac Promoters

| Promoter | Inducer |
|---|---|
| $P_R$ | High temperature |
| $P_L$ | High temperature |
| Pm | Alkyl- or halo-benzoates |
| Pu | Alkyl- or halo-toluenes |
| Psal | Salicylates |

See, e.g.: J. Sanchez-Romero & V. De Lorenzo (1999) Manual of Industrial Microbiology and Biotechnology (A. Demain & J. Davies, eds.) pp. 460-74 (ASM Press, Washington, D.C.); H. Schweizer (2001) Current Opinion in Biotechnology, 12:439-445; and R. Slater & R. Williams (2000 Molecular Biology and Biotechnology (J. Walker & R. Rapley, eds.) pp. 125-54 (The Royal Society of Chemistry, Cambridge, UK)). A promoter having the nucleotide sequence of a promoter native to the selected bacterial host cell also may be used to control expression of the transgene encoding the target polypeptide, e.g, a *Pseudomonas* anthranilate or benzoate operon promoter (Pant, Pben). Tandem promoters may also be used in which more than one promoter is covalently attached to another, whether the same or different in sequence, e.g., a Pant-Pben tandem promoter (interpromoter hybrid) or a Plac-Plac tandem promoter, or whether derived from the same or different organisms.

Regulated promoters utilize promoter regulatory proteins in order to control transcription of the gene of which the promoter is a part. Where a regulated promoter is used herein, a corresponding promoter regulatory protein will also be part of an expression system according to the present invention. Examples of promoter regulatory proteins include: activator proteins, e.g., *E. coli* catabolite activator protein, MalT protein; AraC family transcriptional activators; repressor proteins, e.g., *E. coli* LacI proteins; and dual-function regulatory proteins, e.g., *E. coli* NagC protein. Many regulated-promoter/promoter-regulatory-protein pairs are known in the art. In one embodiment, the expression construct for the target protein(s) and the heterologous protein of interest are under the control of the same regulatory element.

Promoter regulatory proteins interact with an effector compound, i.e., a compound that reversibly or irreversibly associates with the regulatory protein so as to enable the protein to either release or bind to at least one DNA transcription regulatory region of the gene that is under the control of the promoter, thereby permitting or blocking the action of a transcriptase enzyme in initiating transcription of the gene. Effector compounds are classified as either inducers or co-repressors, and these compounds include native effector compounds and gratuitous inducer compounds. Many regulated-promoter/promoter-regulatory-protein/effector-compound trios are known in the art. Although an effector compound can be used throughout the cell culture or fermentation, in a preferred embodiment in which a regulated promoter is used, after growth of a desired quantity or density of host cell biomass, an appropriate effector compound is added to the culture to directly or indirectly result in expression of the desired gene(s) encoding the protein or polypeptide of interest.

In embodiments wherein a lac family promoter is utilized, a lad gene can also be present in the system. The lad gene, which is normally a constitutively expressed gene, encodes the Lac repressor protein LacI protein, which binds to the lac operator of lac family promoters. Thus, where a lac family promoter is utilized, the lad gene can also be included and expressed in the expression system.

Promoter systems useful in *Pseudomonas* are described in the literature, e.g., in U.S. Pat. App. Pub. No. 2008/0269070, also referenced above.

Other Regulatory Elements

In embodiments, soluble recombinant hG-CSF is present in either the cytoplasm or periplasm of the cell during production. Secretion leaders useful for targeting proteins, e.g., hG-CSF, are described elsewhere herein, and in U.S. Pat. App. Pub. No. 2008/0193974, U.S. Pat. App. Pub. No. 2006/0008877, and in U.S. patent application Ser. No. 12/610,207, referenced above. Examples of secretion leaders that can be used in the methods of the provided invention are shown in Table 3. U.S. Pat. No. 7,070,989 describes a method for secreting G-CSF into the periplasm of an *E. coli* cell. In some embodiments, expression constructs are provided that encode hG-CSF fused to a secretion leader that can transport hG-CSF to the periplasm of a *Pseudomonas* cell. In some embodiments, the secretion leader the secretion leader is cleaved from the hG-CSF protein. In some embodiments, the secretion leader facilitates production of soluble hG-CSF comprising an N-terminal methionine (Met-G-CSF).

An expression construct useful in practicing the methods of the present invention can include, in addition to the protein coding sequence, the following regulatory elements operably linked thereto: a promoter, a ribosome binding site (RBS), a transcription terminator, and translational start and stop signals. Useful RBSs can be obtained from any of the species useful as host cells in expression systems according to, e.g., U.S. Pat. App. Pub. No. 2008/0269070 and U.S. patent application Ser. No. 12/610,207. Many specific and a variety of consensus RBSs are known, e.g., those described in and referenced by D. Frishman et al., Gene 234(2):257-65 (8 Jul. 1999); and B. E. Suzek et al., Bioinformatics 17(12):1123-30 (December 2001). In addition, either native or synthetic RBSs may be used, e.g., those described in: EP 0207459 (synthetic RBSs); O. Ikehata et al., Eur. J. Biochem. 181(3):563-70 (1989) (native RBS sequence of AAGGAAG). Further examples of methods, vectors, and translation and transcription elements, and other elements useful in the present invention are described in, e.g.: U.S. Pat. No. 5,055,294 to Gilroy and U.S. Pat. No. 5,128,130 to Gilroy et al.; U.S. Pat. No. 5,281,532 to Rammler et al.; U.S. Pat. Nos. 4,695,455 and 4,861,595 to Barnes et al.; U.S. Pat. No. 4,755,465 to Gray et al.; and U.S. Pat. No. 5,169,760 to Wilcox.

Host Strains

Bacterial hosts, including *Pseudomonads*, and closely related bacterial organisms are contemplated for use in practicing the methods of the invention. In certain embodiments, the *Pseudomonad* host cell is *Pseudomonas fluorescens*. The host cell can also be an *E. coli* cell.

Host cells and constructs useful in practicing the methods of the invention can be identified or made using reagents and methods known in the art and described in the literature, e.g., in U.S. Pat. App. Pub. No. 2009/0325230, "Protein Expression Systems," incorporated herein by reference in its entirety. This publication describes production of a recombinant polypeptide by introduction of a nucleic acid construct into an auxotrophic *Pseudomonas fluorescens* host cell comprising a chromosomal lacI gene insert. The nucleic acid construct comprises a nucleotide sequence encoding the recombinant polypeptide operably linked to a promoter capable of directing expression of the nucleic acid in the host cell, and also comprises a nucleotide sequence encoding an auxotrophic selection marker. The auxotrophic selection marker is a polypeptide that restores prototrophy to the auxotrophic host cell. In embodiments, the cell is auxotrophic for proline, uracil, or combinations thereof. In embodiments, the host cell is derived from MB101 (ATCC deposit PTA-7841). U.S. Pat. App. Pub. No. 2009/0325230, "Protein Expression Systems," and in Schneider, et al., 2005, "Auxotrophic markers pyrF and proC can replace antibiotic markers on protein production plasmids in high-cell-density *Pseudomonas fluorescens* fermentation," Biotechnol. Progress 21(2): 343-8, both incorporated herein by reference in their entirety, describe a production host strain auxotrophic for uracil that was constructed by deleting the pyrF gene in strain MB 101. The pyrF gene was cloned from strain MB214 (ATCC deposit PTA-7840) to generate a plasmid that can complement the pyrF deletion to restore prototrophy. In particular embodiments, a dual pyrF-proC dual auxotrophic selection marker system in a *P. fluorescens* host cell is used. A PyrF production host strain as described can be used as the background for introducing other desired genomic changes, including those described herein as useful in practicing the methods of the invention.

In embodiments, the host cell is of the order Pseudomonadales. Where the host cell is of the order Pseudomonadales, it may be a member of the family Pseudomonadaceae, including the genus *Pseudomonas*. Gamma Proteobacterial hosts include members of the species *Escherichia coli* and members of the species *Pseudomonas fluorescens*.

Other *Pseudomonas* organisms may also be useful. *Pseudomonads* and closely related species include Gram-negative Proteobacteria Subgroup 1, which include the group of Proteobacteria belonging to the families and/or genera described as "Gram-Negative Aerobic Rods and Cocci" by R. E. Buchanan and N. E. Gibbons (eds.), Bergey's Manual of Determinative Bacteriology, pp. 217-289 (8th ed., 1974) (The Williams & Wilkins Co., Baltimore, Md., USA) (hereinafter "Bergey (1974)"). Table 2 presents these families and genera of organisms.

TABLE 2

| Families and Genera Listed in the Part, "Gram-Negative Aerobic Rods and Cocci" (in Bergey (1974)) | |
| --- | --- |
| Family I. *Pseudomonaceae* | *Gluconobacter* |
| | *Pseudomonas* |
| | *Xanthomonas* |
| | *Zoogloea* |
| Family II. *Azotobacteraceae* | *Azomonas* |
| | *Azotobacter* |
| | *Beijerinckia* |
| | *Derxia* |

TABLE 2-continued

| Families and Genera Listed in the Part, "Gram-Negative Aerobic Rods and Cocci" (in Bergey (1974)) | |
| --- | --- |
| Family III. *Rhizobiaceae* | *Agrobacterium* |
| | *Rhizobium* |
| Family IV. *Methylomonadaceae* | *Methylococcus* |
| | *Methylomonas* |
| Family V. *Halobacteriaceae* | *Halobacterium* |
| | *Halococcus* |
| Other Genera | *Acetobacter* |
| | *Alcaligenes* |
| | *Bordetella* |
| | *Brucella* |
| | *Francisella* |
| | *Thermus* |

*Pseudomonas* and closely related bacteria are generally part of the group defined as "Gram(-) Proteobacteria Subgroup 1" or "Gram-Negative Aerobic Rods and Cocci" (Buchanan and Gibbons (eds.) (1974) Bergey's Manual of Determinative Bacteriology, pp. 217-289). *Pseudomonas* host strains are described in the literature, e.g., in U.S. Pat. App. Pub. No. 2006/0040352, cited above.

"Gram-negative Proteobacteria Subgroup 1" also includes Proteobacteria that would be classified in this heading according to the criteria used in the classification. The heading also includes groups that were previously classified in this section but are no longer, such as the genera *Acidovorax, Brevundimonas, Burkholderia, Hydrogenophaga, Oceanimonas, Ralstonia,* and *Stenotrophomonas*, the genus *Sphingomonas* (and the genus *Blastomonas*, derived therefrom), which was created by regrouping organisms belonging to (and previously called species of) the genus *Xanthomonas*, the genus *Acidomonas*, which was created by regrouping organisms belonging to the genus *Acetobacter* as defined in Bergey (1974). In addition hosts can include cells from the genus *Pseudomonas, Pseudomonas enalia* (ATCC 14393), *Pseudomonas nigrifaciensi* (ATCC 19375), and *Pseudomonas putrefaciens* (ATCC 8071), which have been reclassified respectively as *Alteromonas haloplanktis, Alteromonas nigrifaciens,* and *Alteromonas putrefaciens*. Similarly, e.g., *Pseudomonas acidovorans* (ATCC 15668) and *Pseudomonas testosteroni* (ATCC 11996) have since been reclassified as *Comamonas acidovorans* and *Comamonas testosteroni*, respectively; and *Pseudomonas nigrifaciens* (ATCC 19375) and *Pseudomonas piscicida* (ATCC 15057) have been reclassified respectively as *Pseudoalteromonas nigrifaciens* and *Pseudoalteromonas piscicida*. "Gram-negative Proteobacteria Subgroup 1" also includes Proteobacteria classified as belonging to any of the families: Pseudomonadaceae, Azotobacteraceae (now often called by the synonym, the "*Azotobacter* group" of Pseudomonadaceae), Rhizobiaceae, and Methylomonadaceae (now often called by the synonym, "Methylococcaceae"). Consequently, in addition to those genera otherwise described herein, further Proteobacterial genera falling within "Gram-negative Proteobacteria Subgroup 1" include: 1) *Azotobacter* group bacteria of the genus *Azorhizophilus*; 2) Pseudomonadaceae family bacteria of the genera *Cellvibrio, Oligella,* and *Teredinibacter*; 3) Rhizobiaceae family bacteria of the genera *Chelatobacter, Ensifer, Liberibacter* (also called "*Candidatus Liberibacter*"), and *Sinorhizobium*; and 4) Methylococcaceae family bacteria of the genera *Methylobacter, Methylocaldum, Methylomicrobium, Methylosarcina,* and *Methylosphaera*.

The host cell can be selected from "Gram-negative Proteobacteria Subgroup 16." "Gram-negative Proteobacteria Subgroup 16" is defined as the group of Proteobacteria of the following *Pseudomonas* species (with the ATCC or other deposit numbers of exemplary strain(s) shown in parenthesis): *Pseudomonas abietaniphila* (ATCC 700689); *Pseudomonas aeruginosa* (ATCC 10145); *Pseudomonas alcaligenes* (ATCC 14909); *Pseudomonas anguilliseptica* (ATCC 33660); *Pseudomonas citronellolis* (ATCC 13674); *Pseudomonas flavescens* (ATCC 51555); *Pseudomonas mendocina* (ATCC 25411); *Pseudomonas nitroreducens* (ATCC 33634); *Pseudomonas oleovorans* (ATCC 8062); *Pseudomonas pseudoalcaligenes* (ATCC 17440); *Pseudomonas resinovorans* (ATCC 14235); *Pseudomonas straminea* (ATCC 33636); *Pseudomonas agarici* (ATCC 25941); *Pseudomonas alcaliphila*; *Pseudomonas alginovora*; *Pseudomonas andersonii*; *Pseudomonas asplenii* (ATCC 23835); *Pseudomonas azelaica* (ATCC 27162); *Pseudomonas beyerinckii* (ATCC 19372); *Pseudomonas borealis*; *Pseudomonas boreopolis* (ATCC 33662); *Pseudomonas brassicacearum*; *Pseudomonas butanovora* (ATCC 43655); *Pseudomonas cellulosa* (ATCC 55703); *Pseudomonas aurantiaca* (ATCC 33663); *Pseudomonas chlororaphis* (ATCC 9446, ATCC 13985, ATCC 17418, ATCC 17461); *Pseudomonas fragi* (ATCC 4973); *Pseudomonas lundensis* (ATCC 49968); *Pseudomonas taetrolens* (ATCC 4683); *Pseudomonas cissicola* (ATCC 33616); *Pseudomonas coronafaciens*; *Pseudomonas diterpeniphila*; *Pseudomonas elongata* (ATCC 10143); *Pseudomonas flectens* (ATCC 12775); *Pseudomonas azotoformans*; *Pseudomonas brenneri*; *Pseudomonas cedrella*; *Pseudomonas corrugata* (ATCC 29736); *Pseudomonas extremorientalis*; *Pseudomonas fluorescens* (ATCC 35858); *Pseudomonas gessardii*; *Pseudomonas libanensis*; *Pseudomonas mandelii* (ATCC 700871); *Pseudomonas marginalis* (ATCC 10844); *Pseudomonas migulae*; *Pseudomonas mucidolens* (ATCC 4685); *Pseudomonas orientalis*; *Pseudomonas rhodesiae*; *Pseudomonas synxantha* (ATCC 9890); *Pseudomonas tolaasii* (ATCC 33618); *Pseudomonas veronii* (ATCC 700474); *Pseudomonas frederiksbergensis*; *Pseudomonas geniculata* (ATCC 19374); *Pseudomonas gingeri*; *Pseudomonas graminis*; *Pseudomonas grimontii*; *Pseudomonas halodenitrificans*; *Pseudomonas halophila*; *Pseudomonas hibiscicola* (ATCC 19867); *Pseudomonas huttiensis* (ATCC 14670); *Pseudomonas hydrogenovora*; *Pseudomonas jessenii* (ATCC 700870); *Pseudomonas kilonensis*; *Pseudomonas lanceolata* (ATCC 14669); *Pseudomonas lini*; *Pseudomonas marginate* (ATCC 25417); *Pseudomonas mephitica* (ATCC 33665); *Pseudomonas denitrificans* (ATCC 19244); *Pseudomonas pertucinogena* (ATCC 190); *Pseudomonas pictorum* (ATCC 23328); *Pseudomonas psychrophila*; *Pseudomonas filva* (ATCC 31418); *Pseudomonas monteilii* (ATCC 700476); *Pseudomonas mosselii*; *Pseudomonas oryzihabitans* (ATCC 43272); *Pseudomonas plecoglossicida* (ATCC 700383); *Pseudomonas putida* (ATCC 12633); *Pseudomonas reactans*; *Pseudomonas spinosa* (ATCC 14606); *Pseudomonas balearica*; *Pseudomonas luteola* (ATCC 43273); *Pseudomonas stutzeri* (ATCC 17588); *Pseudomonas amygdali* (ATCC 33614); *Pseudomonas avellanae* (ATCC 700331); *Pseudomonas caricapapayae* (ATCC 33615); *Pseudomonas cichorii* (ATCC 10857); *Pseudomonas ficuserectae* (ATCC 35104); *Pseudomonas fuscovaginae*; *Pseudomonas meliae* (ATCC 33050); *Pseudomonas syringae* (ATCC 19310); *Pseudomonas viridiflava* (ATCC 13223); *Pseudomonas thermocarboxydovorans* (ATCC 35961); *Pseudomonas thermotolerans*; *Pseudomonas thivervalensis*; *Pseudomonas vancouverensis* (ATCC 700688); *Pseudomonas wisconsinensis*; and *Pseudomonas xiamenensis*. In one embodiment, the host cell for expression of hG-CSF is *Pseudomonas fluorescens*.

The host cell can also be selected from "Gram-negative Proteobacteria Subgroup 17." "Gram-negative Proteobacteria Subgroup 17" is defined as the group of Proteobacteria known in the art as the "fluorescent *Pseudomonads*" including those belonging, e.g., to the following *Pseudomonas* species: *Pseudomonas azotoformans*; *Pseudomonas brenneri*; *Pseudomonas cedrella*; *Pseudomonas corrugata*; *Pseudomonas extremorientalis*; *Pseudomonas fluorescens*; *Pseudomonas gessardii*; *Pseudomonas libanensis*; *Pseudomonas mandelii*; *Pseudomonas marginalis*; *Pseudomonas migulae*; *Pseudomonas mucidolens*; *Pseudomonas orientalis*; *Pseudomonas rhodesiae*; *Pseudomonas synxantha*; *Pseudomonas tolaasii*; and *Pseudomonas veronii*.

Proteases

In one embodiment, the methods of the provided invention comprise using a *Pseudomonas* host cell, comprising one or more mutations (e.g., a partial or complete deletion) in one or more protease genes, to produce recombinant hG-CSF protein. In some embodiments, a mutation in a protease gene can facilitate generation of recombinant hG-CSF protein comprising an intact methionine at the N-terminus (Met-G-CSF).

Exemplary target protease genes include those proteases classified as Aminopeptidases; Dipeptidases; Dipeptidyl-peptidases and tripeptidyl peptidases; Peptidyl-dipeptidases; Serine-type carboxypeptidases; Metallocarboxypeptidases; Cysteine-type carboxypeptidases; Omegapeptidases; Serine proteinases; Cysteine proteinases; Aspartic proteinases; Metallo proteinases; or Proteinases of unknown mechanism.

Aminopeptidases include cytosol aminopeptidase (leucyl aminopeptidase), membrane alanyl aminopeptidase, cystinyl aminopeptidase, tripeptide aminopeptidase, prolyl aminopeptidase, arginyl aminopeptidase, glutamyl aminopeptidase, x-pro aminopeptidase, bacterial leucyl aminopeptidase, thermophilic aminopeptidase, clostridial aminopeptidase, cytosol alanyl aminopeptidase, lysyl aminopeptidase, x-trp aminopeptidase, tryptophanyl aminopeptidase, methionyl aminopeptidas, d-stereospecific aminopeptidase, aminopeptidase ey. Dipeptidases include x-his dipeptidase, x-arg dipeptidase, x-methyl-his dipeptidase, cys-gly dipeptidase, glu-glu dipeptidase, pro-x dipeptidase, x-pro dipeptidase, met-x dipeptidase, non-stereospecific dipeptidase, cytosol non-specific dipeptidase, membrane dipeptidase, beta-ala-his dipeptidase. Dipeptidyl-peptidases and tripeptidyl peptidases include dipeptidyl-peptidase i, dipeptidyl-peptidase ii, dipeptidyl peptidase iii, dipeptidyl-peptidase iv, dipeptidyl-dipeptidase, tripeptidyl-peptidase I, tripeptidyl-peptidase II. Peptidyl-dipeptidases include peptidyl-dipeptidase a and peptidyl-dipeptidase b. Serine-type carboxypeptidases include lysosomal pro-x carboxypeptidase, serine-type D-ala-D-ala carboxypeptidase, carboxypeptidase C, carboxypeptidase D. Metallocarboxypeptidases include carboxypeptidase a, carboxypeptidase B, lysine(arginine) carboxypeptidase, gly-X carboxypeptidase, alanine carboxypeptidase, muramoylpentapeptide carboxypeptidase, carboxypeptidase h, glutamate carboxypeptidase, carboxypeptidase M, muramoyltetrapeptide carboxypeptidase, zinc d-ala-d-ala carboxypeptidase, carboxypeptidase A2, membrane pro-x carboxypeptidase, tubulinyl-tyr carboxypeptidase, carboxypeptidase t. Omega-peptidases include acylaminoacyl-peptidase, peptidyl-glycinamidase, pyroglutamyl-peptidase I, beta-aspartyl-peptidase, pyroglutamyl-peptidase II, n-formylmethionyl-peptidase, pteroylpoly-[gamma]-glutamate carboxypeptidase, gamma-glu-X carboxypeptidase, acylmuramoyl-ala peptidase. Serine proteinases include chymotrypsin, chymotrypsin c, metridin, trypsin, thrombin, coagulation factor Xa, plasmin, enteropeptidase, acrosin, alpha-lytic protease, glutamyl, endopeptidase, cathepsin G, coagulation factor viia, coagulation factor ixa, cucumisi, prolyl oligopeptidase, coagulation factor xia, brachyurin, plasma kallikrein, tissue kallikrein, pancreatic elastase, leukocyte elastase, coagulation factor xiia, chymase, complement component c1r55, complement component c1s55, classical-complement pathway c3/c5 convertase, complement factor I, complement factor D, alternative-complement pathway c3/c5 convertase, cerevisin, hypodermin C, lysyl endopeptidase, endopeptidase 1a, gamma-reni, venombin ab, leucyl endopeptidase, tryptase, scutelarin, kexin, subtilisin, oryzin, endopeptidase k, thermomycolin, thermitase, endopeptidase SO, T-plasminogen activator, protein C, pancreatic endopeptidase E, pancreatic elastase ii, IGA-specific serine endopeptidase, U-plasminogen, activator, venombin A, furin, myeloblastin, semenogelase, granzyme A or cytotoxic T-lymphocyte proteinase 1, granzyme B or cytotoxic T-lymphocyte proteinase 2, streptogrisin A, treptogrisin B, glutamyl endopeptidase II, oligopeptidase B, limulus clotting factor c, limulus clotting factor, limulus clotting enzyme, omptin, repressor lexa, bacterial leader peptidase I, togavirin, flavirin. Cysteine proteinases include cathepsin B, papain, ficin, chymopapain, asclepain, clostripain, streptopain, actinide, cathepsin 1, cathepsin H, calpain, cathepsin t, glycyl, endopeptidase, cancer procoagulant, cathepsin S, picornain 3C, picornain 2A, caricain, ananain, stem bromelain, fruit bromelain, legumain, histolysain, interleukin 1-beta converting enzyme. Aspartic proteinases include pepsin A, pepsin B, gastricsin, chymosin, cathepsin D, neopenthesin, renin, retropepsin, pro-opiomelanocortin converting enzyme, aspergillopepsin I, aspergillopepsin II, penicillopepsin, rhizopuspepsin, endothiapepsin, mucoropepsin, candidapepsin, saccharopepsin, rhodotorulapepsin, physaropepsin, acrocylindropepsin, polyporopepsin, pycnoporopepsin, scytalidopepsin a, scytalidopepsin b, xanthomonapepsin, cathepsin e, barrierpepsin, bacterial leader peptidase I, pseudomonapepsin, plasmepsin. Metallo proteinases include atrolysin a, microbial collagenase, leucolysin, interstitial collagenase, neprilysin, envelysin, iga-specific metalloendopeptidase, procollagen N-endopeptidase, thimet oligopeptidase, neurolysin, stromelysin 1, meprin A, procollagen C-endopeptidase, peptidyl-lys metalloendopeptidase, astacin, stromelysin, 2, matrilysin gelatinase, aeromonolysin, pseudo lysin, thermolysin, bacillolysin, aureolysin, coccolysin, mycolysin, beta-lytic metalloendopeptidase, peptidyl-asp metalloendopeptidase, neutrophil collagenase, gelatinase B, leishmanolysin, saccharolysin, autolysin, deuterolysin, serralysin, atrolysin B, atrolysin C, atroxase, atrolysin E, atrolysin F, adamalysin, horrilysin, ruberlysin, bothropasin, bothrolysin, ophiolysin, trimerelysin I, trimerelysin II, mucrolysin, pitrilysin, insulysin, O-syaloglycoprotein endopeptidase, russellysin, mitochondrial, intermediate, peptidase, dactylysin, nardilysin, magnolysin, meprin B, mitochondrial processing peptidase, macrophage elastase, choriolysin, toxilysin. Proteinases of unknown mechanism include thermopsin and multicatalytic endopeptidase complex.

Certain proteases can have both protease and chaperone-like activity. When these proteases are negatively affecting protein yield and/or quality it can be useful to specifically delete their protease activity, and they can be overexpressed when their chaperone activity may positively affect protein yield and/or quality. These proteases include, but are not limited to: Hsp100(Clp/Hsl) family members RXF04587.1 (clpA), RXF08347.1, RXF04654.2 (clpX), RXF04663.1, RXF01957.2 (hslU), RXF01961.2 (hslV); Peptidyl-prolyl cis-trans isomerase family member RXF05345.2 (ppiB); Metallopeptidase M20 family member RXF04892.1 (aminohydrolase); Metallopeptidase M24 family members RXF04693.1 (methionine aminopeptidase) and RXF03364.1 (methionine aminopeptidase); and Serine Peptidase S26 signal peptidase I family member RXF01181.1 (signal peptidase).

Codon Optimization

In one embodiment, the methods of the provided invention comprise expression of recombinant hG-CSF from a construct that has been optimized for codon usage in a strain of interest. In embodiments, the strain is a *Pseudomonas* host cell, e.g., *Pseudomonas fluorescens*. Methods for optimizing codons to improve expression in bacterial hosts are known in the art and described in the literature. For example, optimization of codons for expression in a *Pseudomonas* host strain is described, e.g., in U.S. Pat. App. Pub. No. 2007/0292918, "Codon Optimization Method," incorporated herein by reference in its entirety.

In heterologous expression systems, optimization steps may improve the ability of the host to produce the foreign protein. Protein expression is governed by a host of factors including those that affect transcription, mRNA processing, and stability and initiation of translation. The polynucleotide optimization steps may include steps to improve the ability of the host to produce the foreign protein as well as steps to assist the researcher in efficiently designing expression constructs. Optimization strategies may include, for example, the modification of translation initiation regions, alteration of mRNA structural elements, and the use of different codon biases. Methods for optimizing the nucleic acid sequence of to improve expression of a heterologous protein in a bacterial host are known in the art and described in the literature. For example, optimization of codons for expression in a *Pseudomonas* host strain is described, e.g., in U.S. Pat. App. Pub. No. 2007/0292918, "Codon Optimization Method," incorporated herein by reference in its entirety.

Optimization can thus address any of a number of sequence features of the heterologous gene. As a specific example, a rare codon-induced translational pause can result in reduced heterologous protein expression. A rare codon-induced translational pause includes the presence of codons in the polynucleotide of interest that are rarely used in the host organism may have a negative effect on protein translation due to their scarcity in the available tRNA pool. One method of improving optimal translation in the host organism includes performing codon optimization which can result in rare host codons being removed from the synthetic polynucleotide sequence.

Alternate translational initiation also can result in reduced heterologous protein expression. Alternate translational initiation can include a synthetic polynucleotide sequence inadvertently containing motifs capable of functioning as a ribosome binding site (RBS). These sites can result in initiating translation of a truncated protein from a gene-internal site. One method of reducing the possibility of producing a truncated protein, which can be difficult to remove during purification, includes eliminating putative internal RBS sequences from an optimized polynucleotide sequence.

Repeat-induced polymerase slippage can result in reduced heterologous protein expression. Repeat-induced polymerase slippage involves nucleotide sequence repeats that have been shown to cause slippage or stuttering of DNA polymerase which can result in frameshift mutations. Such repeats can also cause slippage of RNA polymerase. In an organism with a high G+C content bias, there can be a higher degree of repeats composed of G or C nucleotide repeats. Therefore, one method of reducing the possibility of inducing RNA polymerase slippage, includes altering extended repeats of G or C nucleotides.

Interfering secondary structures also can result in reduced heterologous protein expression. Secondary structures can sequester the RBS sequence or initiation codon and have been correlated to a reduction in protein expression. Stemloop structures can also be involved in transcriptional pausing and attenuation. An optimized polynucleotide sequence can contain minimal secondary structures in the RBS and gene coding regions of the nucleotide sequence to allow for improved transcription and translation.

Another feature that can effect heterologous protein expression is the presence of restriction sites. By removing restriction sites that could interfere with subsequent subcloning of transcription units into host expression vectors a polynucleotide sequence can be optimized.

For example, the optimization process can begin by identifying the desired amino acid sequence to be heterologously expressed by the host. From the amino acid sequence a candidate polynucleotide or DNA sequence can be designed. During the design of the synthetic DNA sequence, the frequency of codon usage can be compared to the codon usage of the host expression organism and rare host codons can be removed from the synthetic sequence. Additionally, the synthetic candidate DNA sequence can be modified in order to remove undesirable enzyme restriction sites and add or remove any desired signal sequences, linkers or untranslated regions. The synthetic DNA sequence can be analyzed for the presence of secondary structure that may interfere with the translation process, such as G/C repeats and stem-loop structures. Before the candidate DNA sequence is synthesized, the optimized sequence design can be checked to verify that the sequence correctly encodes the desired amino acid sequence. Finally, the candidate DNA sequence can be synthesized using DNA synthesis techniques, such as those known in the art.

In another embodiment of the invention, the general codon usage in a host organism, such as *P. fluorescens*, can be utilized to optimize the expression of the heterologous polynucleotide sequence. The percentage and distribution of codons that rarely would be considered as preferred for a particular amino acid in the host expression system can be evaluated. Values of 5% and 10% usage can be used as cutoff values for the determination of rare codons. For example, the codons listed in Table 3 have a calculated occurrence of less than 5% in the *P. fluorescens* MB214 genome and would be generally avoided in an optimized gene expressed in a *P. fluorescens* host.

TABLE 3

Codons occurring at less than 5% in *P. fluorescens* MB214

| Amino Acid(s) | Codon(s) Used | % Occurrence |
| --- | --- | --- |
| G Gly | GGA | 3.26 |
| I Ile | ATA | 3.05 |
| L Leu | CTA | 1.78 |
|  | CTT | 4.57 |
|  | TTA | 1.89 |
| R Arg | AGA | 1.39 |
|  | AGG | 2.72 |
|  | CGA | 4.99 |
| S Ser | TCT | 4.28 |

The present invention contemplates the use of any GCSF coding sequence, including any sequence that has been optimized for expression in the *Pseudomonas* host cell being used. Sequences contemplated for use can be optimized to any degree as desired, including, but not limited to, optimization to eliminate: codons occurring at less than 5% in the *Pseudomonas* host cell, codons occurring at less than 10% in the *Pseudomonas* host cell, a rare codon-induced translational pause, a putative internal RBS sequence, an extended repeat of G or C nucleotides, an interfering secondary structure, a restriction site, or combinations thereof.

Furthermore, the amino acid sequence of any secretion leader useful in practicing the methods of the present invention can be encoded by any appropriate nucleic acid sequence. Codon optimization for expression in *E. coli* is described, e.g., by Welch, et al., 2009, PLoS One, "Design Parameters to Control Synthetic Gene Expression in *Escherichia coli*," 4(9): e7002, Ghane, et al., 2008, Krishna R. et al., (2008) Mol Biotechnology "Optimization of the AT-content of Codons Immediately Downstream of the Initiation Codon and Evaluation of Culture Conditions for High-level Expression of Recombinant Human G-CSF in *Escherichia coli*," 38:221-232.

High Throughput Screens

In some embodiments, a high throughput screen can be conducted to determine optimal conditions for expressing soluble recombinant hG-CSF. In some embodiments, a high throughput screen can be conducted to determine optimal conditions for expressing soluble recombinant hG-CSF comprising an N-terminal methionine (Met-G-CSF). The conditions that be varied in the screen include, for example, the host cell, genetic background of the host cell (e.g., deletions of different proteases), type of promoter in an expression construct, type of secretion leader fused to encoded hG-CSF, temperature of growth, OD of induction when an inducible promoter is used, amount of IPTG used for induction when a lacZ promoter is used, duration of protein induction, temperature of growth following addition of an inducing agent to a culture, rate of agitation of culture, method of selection for plasmid maintenance, volume of culture in a vessel, and method of cell lysing.

In some embodiments, a library (or "array") of host strains is provided, wherein each strain (or "population of host cells") in the library has been genetically modified to modulate the expression of one or more target genes in the host cell. An "optimal host strain" or "optimal expression system" can be identified or selected based on the quantity, quality, and/or location of the expressed protein of interest compared to other populations of phenotypically distinct host cells in the array. Thus, an optimal host strain is the strain that produces the polypeptide of interest according to a desired specification. While the desired specification will vary depending on the polypeptide being produced, the specification includes the quality and/or quantity of protein, whether the protein is sequestered or secreted, protein folding, and the like. For example, the optimal host strain or optimal expression system produces a yield, characterized by the amount of soluble heterologous protein, the amount of recoverable heterologous protein, the amount of properly processed heterologous protein, the amount of properly folded heterologous protein, the amount of active heterologous protein, and/or the total amount of heterologous protein, of a certain absolute level or a certain level relative to that produced by an indicator strain, i.e., a strain used for comparison.

Methods of screening microbial hosts to identify strains with improved yield and/or quality in the expression of heterologous proteins are described, for example, in U.S. Patent Application Publication No. 20080269070.

Bacterial Growth Conditions

Growth conditions useful in the methods of the provided invention can comprise a temperature of about 4° C. to about 42° C. and a pH of about 5.7 to about 8.8. When an expression construct with a lacZ promoter is used, expression can be induced by adding IPTG to a culture at a final concentration of about 0.01 mM to about 1.0 mM.

The pH of the culture can be maintained using pH buffers and methods known to those of skill in the art. Control of pH during culturing also can be achieved using aqueous ammonia. In embodiments, the pH of the culture is about 5.7 to about 8.8. In certain embodiments, the pH is about 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, or 8.8 In other embodiments, the pH is about 5.7 to 5.9, 5.8 to 6.0, 5.9 to 6.1, 6.0 to 6.2, 6.1 to 6.3, 6.2 to 6.5, 6.4 to 6.7, 6.5 to 6.8, 6.6 to 6.9, 6.7 to 7.0, 6.8 to 7.1, 6.9 to 7.2, 7.0 to 7.3, 7.1 to 7.4, 7.2 to 7.5, 7.3 to 7.6, 7.4 to 7.7, 7.5 to 7.8, 7.6 to 7.9, 7.7 to 8.0, 7.8 to 8.1, 7.9 to 8.2, 8.0 to 8.3, 8.1 to 8.4, 8.2 to 8.5, 8.3 to 8.6, 8.4 to 8.7, or 8.5 to 8.8. In yet other embodiments, the pH is about 5.7 to 6.0, 5.8 to 6.1, 5.9 to 6.2, 6.0 to 6.3, 6.1 to 6.4, or 6.2 to 6.5. In certain embodiments, the pH is about 5.7 to about 6.25.

In embodiments, the growth temperature is maintained at about 4° C. to about 42° C. In certain embodiments, the growth temperature is about 4° C., about 5° C., about 6° C., about 7° C., about 8° C., about 9° C., about 10° C., about 11° C., about 12° C., about 13° C., about 14° C., about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., or about 42° C. In other embodiments, the growth temperature is maintained at about 25° C. to about 27° C., about 25° C. to about 28° C., about 25° C. to about 29° C., about 25° C. to about 30° C., about 25° C. to about 31° C., about 25° C. to about 32° C., about 25° C. to about 33° C., about 26° C. to about 28° C., about 26° C. to about 29° C., about 26° C. to about 30° C., about 26° C. to about 31° C., about 26° C. to about 32° C., about 27° C. to about 29° C., about 27° C. to about 30° C., about 27° C. to about 31° C., about 27° C. to about 32° C., about 26° C. to about 33° C., about 28° C. to about 30° C., about 28° C. to about 31° C., about 28° C. to about 32° C., about 29° C. to about 31° C., about 29° C. to about 32° C., about 29° C. to about 33° C., about 30° C. to about 32° C., about 30° C. to about 33° C., about 31° C. to about 32° C., about 30° C. to about 33° C., or about 32° C. to about 33° C. In other embodiments, the temperature is changed during culturing. In one embodiment, the temperature is maintained at about 30° C. before an agent to induce expression from the construct expressing hG-CSF is added to the culture, and the temperature is dropped to about 25° C. after adding an agent to induce expression, e.g., IPTG is added to the culture.

Induction

As described elsewhere herein, inducible promoters can be used in the expression construct to control expression of the recombinant hG-CSF, e.g., a lac promoter. In the case of the lac promoter derivatives or family members, e.g., the tac promoter, the effector compound is an inducer, such as a gratuitous inducer like IPTG (isopropyl-β-D-1-thiogalactopyranoside, also called "isopropylthiogalactoside"). In embodiments, a lac promoter derivative is used, and hG-CSF expression is induced by the addition of IPTG to a final concentration of about 0.01 mM to about 1.0 mM, when the cell density has reached a level identified by an OD575 of about 80 to about 160. In embodiments, the OD575 at the time of culture induction for hG-CSF can be about 80, about 90, about 100, about 110, about 120, about 130, about 140, about 150, about 160, about 170 about 180.

In other embodiments, the OD575 is about 80 to about 100, about 100 to about 120, about 120 to about 140, about 140 to about 160. In other embodiments, the OD575 is about 80 to about 120, about 100 to about 140, or about 120 to about 160. In other embodiments, the OD575 is about 80 to about 140, or about 100 to 160. The cell density can be measured by other methods and expressed in other units, e.g., in cells per unit volume. For example, an OD575 of about 80 to about 160 of a *Pseudomonas fluorescens* culture is equivalent to approximately $8 \times 10^{10}$ to about $1.6 \times 10^{11}$ colony forming units per mL or 35 to 70 g/L dry cell weight. In embodiments, the cell density at the time of culture induction is equivalent to the cell density as specified herein by the absorbance at OD575, regardless of the method used for determining cell density or the units of measurement. One of skill in the art will know how to make the appropriate conversion for any cell culture.

In embodiments, the final IPTG concentration of the culture is about 0.01 mM, about 0.02 mM, about 0.03 mM, about 0.04 mM, about 0.05 mM, about 0.06 mM, about 0.07 mM, about 0.08 mM, about 0.09 mM, about 0.1 mM, about 0.2 mM, about 0.3 mM, about 0.4 mM, about 0.5 mM, about 0.6 mM, about 0.7 mM, about 0.8 mM, about 0.9 mM, or about 1 mM. In other embodiments, the final IPTG concentration of the culture is about 0.08 mM to about 0.1 mM, about 0.1 mM to about 0.2 mM, 0.2 mM to about 0.3 mM, about 0.3 mM to about 0.4 mM, about 0.2 mM to about 0.4 mM, about 0.08 to about 0.2 mM, or about 0.1 to 1 mM.

In embodiments wherein a non-lac type promoter is used, as described herein and in the literature, other inducers or effectors can be used. In one embodiment, the promoter is a constitutive promoter.

After adding and inducing agent, cultures can be grown for a period of time, for example about 24 hours, during which time the recombinant hG-CSF is expressed. After adding an inducing agent, a culture can be grown for about 1 hr, about 2 hr, about 3 hr, about 4 hr, about 5 hr, about 6 hr, about 7 hr, about 8 hr, about 9 hr, about 10 hr, about 11 hr, about 12 hr, about 13 hr, about 14 hr, about 15 hr, about 16 hr, about 17 hr, about 18 hr, about 19 hr, about 20 hr, about 21 hr, about 22 hr, about 23 hr, about 24 hr, about 36 hr, or about 48 hr. After an inducing agent is added to a culture, the culture can be grown for about 1 to 48 hrs, about 1 to 24 hrs, about 10 to 24 hrs, about 15 to 24 hrs, or about 20 to 24 hrs. Cell cultures can be concentrated by centrifugation, and the culture pellet resuspended in a buffer or solution appropriate for the subsequent lysis procedure.

In embodiments, cells are disrupted using equipment for high pressure mechanical cell disruption (which are available commercially, e.g., Microfluidics Microfluidizer, Constant Cell Disruptor, Niro-Soavi homogenizer or APV-Gaulin homogenizer). Cells expressing hG-CSF can be disrupted, for example, using sonication. Any appropriate method known in the art for lysing cells can be used to release the soluble fraction. For example, in embodiments, chemical and/or enzymatic cell lysis reagents, such as cell-wall lytic enzyme and EDTA, can be used. Use of frozen or previously stored cultures is also contemplated in the methods of the invention. Cultures can be OD-normalized prior to lysis. For example, cells can be normalized to an OD600 of about 10, about 11, about 12, about 13, about 14, about 15, about 16, about 17, about 18, about 19, or about 20.

Centrifugation can be performed using any appropriate equipment and method. Centrifugation of cell culture or lysate for the purposes of separating a soluble fraction from an insoluble fraction is well-known in the art. For example, lysed cells can be centrifuged at 20,800×g for 20 minutes (at 4° C.), and the supernatants removed using manual or automated liquid handling. The pellet (insoluble) fraction is resuspended in a buffered solution, e.g., phosphate buffered saline (PBS), pH 7.4. Resuspension can be carried out using, e.g., equipment such as impellers connected to an overhead mixer, magnetic stir-bars, rocking shakers, etc.

A "soluble fraction," i.e., the soluble supernatant obtained after centrifugation of a lysate, and an "insoluble fraction," i.e., the pellet obtained after centrifugation of a lysate, result from lysing and centrifuging the cultures. These two fractions also can be referred to as a "first soluble fraction" and a "first insoluble fraction," respectively. US Patent Application Publication No. 20050283000 describes means for manipulating G-CSF protein expressed in inclusion bodies from *E. coli*.

Fermentation Format

In one embodiment, fermentation is used in the methods of producing recombinant hG-CSF comprising an N-terminal methionine. The expression system according to the present invention can be cultured in any fermentation format. For example, batch, fed-batch, semi-continuous, and continuous fermentation modes may be employed herein.

In embodiments, the fermentation medium may be selected from among rich media, minimal media, and mineral salts media. In other embodiments either a minimal medium or a mineral salts medium is selected. In certain embodiments, a mineral salts medium is selected.

Mineral salts media consists of mineral salts and a carbon source such as, e.g., glucose, sucrose, or glycerol. Examples of mineral salts media include, e.g., M9 medium, *Pseudomonas* medium (ATCC 179), and Davis and Mingioli medium (see, B D Davis & E S Mingioli (1950) J. Bact. 60:17-28). The mineral salts used to make mineral salts media include those selected from among, e.g., potassium phosphates, ammonium sulfate or chloride, magnesium sulfate or chloride, and trace minerals such as calcium chloride, borate, and sulfates of iron, copper, manganese, and zinc. Typically, no organic nitrogen source, such as peptone, tryptone, amino acids, or a yeast extract, is included in a mineral salts medium. Instead, an inorganic nitrogen source is used and this may be selected from among, e.g., ammonium salts, aqueous ammonia, and gaseous ammonia. A mineral salts medium will typically contain glucose or glycerol as the carbon source. In comparison to mineral salts media, minimal media can also contain mineral salts and a carbon source, but can be supplemented with, e.g., low levels of amino acids, vitamins, peptones, or other ingredients, though these are added at very minimal levels. Media can be prepared using the methods described in the art, e.g., in U.S. Pat. App. Pub. No. 2006/0040352, referenced and incorporated by reference above. Details of cultivation procedures and mineral salts media useful in the methods of the present invention are described by Riesenberg, D et al., 1991, "High cell density cultivation of *Escherichia coli* at controlled specific growth rate," J. Biotechnol. 20 (1):17-27.

Fermentation may be performed at any scale. The expression systems according to the present invention are useful for recombinant protein expression at any scale. Thus, e.g., microliter-scale, milliliter scale, centiliter scale, and deciliter scale fermentation volumes may be used, and 1 Liter scale and larger fermentation volumes can be used.

In embodiments, the fermentation volume is at or above about 1 Liter. In embodiments, the fermentation volume is about 1 liter to about 100 liters. In embodiments, the fermentation volume is about 1 liter, about 2 liters, about 3 liters, about 4 liters, about 5 liters, about 6 liters, about 7 liters, about 8 liters, about 9 liters, or about 10 liters. In embodiments, the fermentation volume is about 1 liter to about 5 liters, about 1 liter to about 10 liters, about 1 liter to about 25 liters, about 1 liter to about 50 liters, about 1 liter to about 75 liters, about 10 liters to about 25 liters, about 25 liters to about 50 liters, or about 50 liters to about 100 liters In other embodiments, the fermentation volume is at or above 5 Liters, 10 Liters, 15 Liters, 20 Liters, 25 Liters, 50 Liters, 75 Liters, 100 Liters, 200 Liters, 500 Liters, 1,000 Liters, 2,000 Liters, 5,000 Liters, 10,000 Liters, or 50,000 Liters.

Protein Analysis

In embodiments, recombinant hG-CSF protein (e.g., Met-G-CSF) produced by the methods of the provided invention is analyzed. Recombinant hG-CSF protein (e.g., Met-G-CSF) can be analyzed, for example, by biolayer interferometry, SDS-PAGE, Western blot, Far Western blot, ELISA, absorbance, or mass spectrometry (e.g., tandem mass spectrometry). The recombinant hG-CSF protein can comprise an N-terminal methionine.

In some embodiments, the concentration and/or amounts of recombinant hG-CSF protein (e.g., Met-G-CSF) generated are determined, for example, by Bradford assay, absorbance, Coosmassie staining, mass spectrometry, etc.

Protein yield in the insoluble and soluble fractions as described herein can be determined by methods known to those of skill in the art, for example, by capillary gel electrophoresis (CGE), and Western blot analysis. Soluble fractions can be evaluated, for example, using biolayer interferometry.

Useful measures of protein yield include, e.g., the amount of recombinant protein per culture volume (e.g., grams or milligrams of protein/liter of culture), percent or fraction of recombinant protein measured in the insoluble pellet obtained after lysis (e.g., amount of recombinant protein in extract supernatant/amount of protein in insoluble fraction), percent or fraction of active protein (e.g., amount of active protein/amount protein used in the assay), percent or fraction of total cell protein (tcp), amount of protein/cell, and percent dry biomass.

In embodiments, the methods of the present invention can be used to obtain a yield of soluble recombinant hG-CSF protein comprising an N-terminal methionine (Met-G-CSF) of about 0.1 grams per liter to about 10 grams per liter. In certain embodiments, the yield of soluble recombinant hG-CSF protein comprising an N-terminal methionine (Met-G-CSF) is about 0.1 grams per liter, about 0.2 grams per liter, about 0.3 grams per liter, about 0.4 grams per liter, about 0.5 grams per liter, about 0.6 grams per liter, about 0.7 grams per liter, about 0.8 grams per liter, about 0.9 grams per liter, about 1 gram per liter, about 2 grams per liter, about 3 grams per liter, about 4 grams per liter, about 5 grams per liter, about 6 grams per liter, about 7 grams per liter, about 8 grams per liter, about 9 grams per liter, about 10 grams per liter, about 0.1 grams per liter to about 0.5 grams per liter, about 0.1 grams to about 1 grams per liter, about 0.1 gram per liter to about 2 grams per liter, about 0.1 grams per liter to about 3 grams per liter, about 0.1 grams per liter to about 4 grams per liter, about 0.1 grams per liter to about 5 grams per liter, about 0.1 grams per liter to about 6 grams per liter, about 0.1 grams per liter to about 7 grams per liter, about 0.1 grams per liter to about 8 grams per liter, about 0.1 grams per liter to about 9 grams per liter, about 0.1 grams per liter to about 10 grams per liter, about 1 gram per liter to about 2 grams per liter, about 2 grams per liter to about 3 grams per liter, about 3 grams per liter to about 4 grams per liter, about 4 grams per liter to about 5 grams per liter, about 5 grams per liter to about 6 grams per liter, about 6 grams per liter to about 7 grams per liter, about 7 grams per liter to about 8 grams per liter, about 8 grams per liter to about 9 grams per liter, or about 9 grams per liter to about 10 grams per liter. In embodiments, the soluble recombinant protein yield is about 1 gram per liter to about 3 grams per liter, about 2 grams per liter to about 4 grams per liter, about 3 grams per liter to about 5 grams per liter, about 4 grams per liter to about 6 grams per liter, about 5 grams per liter to about 7 grams per liter, about 6 grams per liter to about 8 grams per liter, about 7 grams per liter to about 9 grams per liter, or about 8 grams per liter to about 10 grams per liter. In embodiments, the soluble recombinant protein yield is about 0.5 grams per liter to about 4 grams per liter, about 1 gram per liter to about 5 grams per liter, about 2 grams per liter to about 6 grams per liter, about 3 grams per liter to about 7 grams per liter, about 4 grams per liter to about 8 grams per liter, about 5 grams per liter to about 9 grams per liter, or about 6 grams per liter to about 10 grams per liter. In embodiments, the extracted protein yield is about 0.5 grams per liter to about 5 grams per liter, about 0.5 gram per liter to about 10 grams per liter, about 1 grams per liter to about 6 grams per liter, about 2 grams per liter to about 7 grams per liter, about 3 grams per liter to about 8 grams per liter, about 4 grams per liter to about 9 grams per liter, or about 5 grams per liter to about 10 grams per liter.

In embodiments, the amount of recombinant hG-CSF protein comprising an N-terminal methionine (Met-G-CSF) detected in the soluble fraction is about 10% to about 100% of the amount of the total recombinant hG-CSF produced. In embodiments, this amount is about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or about 99%, or about 100% of the amount of the total recombinant hG-CSF produced. In embodiments, this amount is about 10% to about 20%, 20% to about 50%, about 25% to about 50%, about 25% to about 50%, about 25% to about 95%, about 30% to about 50%, about 30% to about 40%, about 30% to about 60%, about 30% to about 70%, about 35% to about 50%, about 35% to about 70%, about 35% to about 75%, about 35% to about 95%, about 40% to about 50%, about 40% to about 95%, about 50% to about 75%, about 50% to about 95%, about 70% to about 95%, or about 80 to about 100% of the amount of the total recombinant hG-CSF produced.

In embodiments, the amount of soluble recombinant hG-CSF protein comprising an N-terminal methionine (Met-G-CSF) produced is about 0.1% to about 50% of the total soluble protein produced in a culture. In embodiments, this amount is more than about 0.1%, 0.5%, 1%, 5%, 10%, 15%, 20%, 25%, 30%, 40%, 45%, or 50% of the total soluble protein produced in a culture. In embodiments, this amount is about 0.1%, 0.5%, 1%, 5%, 10%, 15%, 20%, 25%, 30%, 40%, 45%, or 50% of the total soluble protein produced in a culture. In embodiments, this amount is about 5% to about 50%, about 10% to about 40%, about 20% to about 30%, about 1% to about 20%, about 5% to about 25%, about 1% to about 10%, about 10% to about 20%, about 20% to about 30%, about 30% to about 40%, or about 40% to about 50% of the total soluble protein produced in a culture.

In embodiments, the amount of soluble recombinant hG-CSF protein comprising an N-terminal methionine (Met-G-CSF) produced is about 0.1% to about 50% of the dry cell weight (DCW). In embodiments, this amount is more than about 0.1%, 0.5%, 1%, 5%, 10%, 15%, 20%, 25%, 30%, 40%, 45%, or 50% of DCW. In embodiments, this amount is about 0.1%, 0.5%, 1%, 5%, 10%, 15%, 20%, 25%, 30%, 40%, 45%, or 50% of DCW. In embodiments, this amount is about 5% to about 50%, about 10% to about 40%, about 20% to about 30%, about 1% to about 20%, about 5% to about 30%, about 25%, about 1% to about 10%, about 10% to about 20%, about 20% to about 30%, about 30% to about 40%, or about 40% to about 50% of the total soluble protein produced in a culture.

In embodiments, the recombinant hG-CSF protein comprises an 175 amino acid protein with an N-terminal methionine (Met-G-CSF). In embodiments, the recombinant hG-CSF protein is not glycosylated.

Solubility and Activity

The "solubility" and "activity" of a protein, though related qualities, are generally determined by different means. Solubility of a protein, particularly a hydrophobic protein, indicates that hydrophobic amino acid residues are improperly located on the outside of the folded protein. Protein activity, which can be evaluated using different methods, e.g., as described below, is another indicator of proper protein conformation. "Soluble, active, or both" as used herein, refers to protein that is determined to be soluble, active, or both soluble and active, by methods known to those of skill in the art.

Activity Assay

Assays for evaluating hG-CSF activity are know in the art and can include binding to recombinant human granulocyte colony stimulating factor receptor (GCSF-R). A binding assay is described in Example 1.

In embodiments, activity is represented by the percent active protein in the extract supernatant as compared with the total amount assayed. This is based on the amount of protein determined to be active by the assay relative to the total amount of protein used in assay. In other embodiments, activity is represented by the % activity level of the protein compared to a standard, e.g., native protein. This is based on the amount of active protein in supernatant extract sample relative to the amount of active protein in a standard sample (where the same amount of protein from each sample is used in assay).

In embodiments, about 40% to about 100% of the recombinant hG-CSF protein comprising an N-terminal methionine (Met-G-CSF), is determined to be active. In embodiments, about 40%, about 50%, about 60%, about 70%, about 80%, about 90%, or about 100% of the recombinant hG-CSF protein is determined to be active. In embodiments, about 40% to about 50%, about 50% to about 60%, about 60% to about 70%, about 70% to about 80%, about 80% to about 90%, about 90% to about 100%, about 50% to about 100%, about 60% to about 100%, about 70% to about 100%, about 80% to about 100%, about 40% to about 90%, about 40% to about 95%, about 50% to about 90%, about 50% to about 95%, about 50% to about 100%, about 60% to about 90%, about 60% to about 95%, about 60% to about 100%, about 70% to about 90%, about 70% to about 95%, about 70% to about 100%, or about 70% to about 100% of the recombinant hG-CSF protein comprising an N-terminal methionine (Met-G-CSF) is determined to be active.

In other embodiments, about 75% to about 100% of the recombinant hG-CSF protein comprising an N-terminal methionine (Met-G-CSF) is determined to be active. In embodiments, about 75% to about 80%, about 75% to about 85%, about 75% to about 90%, about 75% to about 95%, about 80% to about 85%, about 80% to about 90%, about 80% to about 95%, about 80% to about 100%, about 85% to about 90%, about 85% to about 95%, about 85% to about 100%, about 90% to about 95%, about 90% to about 100%, or about 95% to about 100% of the recombinant hG-CSF protein comprising an N-terminal methionine (Met-G-CSF) is determined to be active.

EXAMPLE

Example 1

Screening for Met-G-CSF Expression

Design of a Synthetic G-CSF Gene for Optimal Expression.
The following criteria were used for the design of the synthetic G-CSF gene that was optimized for high-level production in *Pseudomonas fluorescens*. A DNA sequence coding for G-CSF (FIG. 6) was designed to reflect appropriate codon usage for *P. fluorescens* strain MB101. A DNA region containing a unique restriction enzyme site (SapI) was added upstream of the GCSF coding sequence designed for direct fusion in frame with the secretion leader present in the expression vector. A DNA region containing 3 stop codons and a unique restriction enzyme site (SapI) was added downstream of the coding sequence. All gene-internal ribosome binding sites which matched the pattern aggaggtn$_{5-10}$dtg with 2 or fewer mismatches were removed to avoid potentially truncated protein products. Stretches of 5 or more C or 5 or more G nucleotides were eliminated to avoid RNA polymerase slippage. Strong gene-internal stem-loop structures, especially those covering the ribosome binding site, were removed. The synthetic gene was produced by DNA2.0 Inc. (Menlo Park, Calif.).

Synthesis the Met-G-CSF Gene by PCR Amplifications

Standard cloning methods were used in the construction of cytoplasmic and periplasmic Met-GCSF expression plasmids. PCR products were generated using Pfusion™ high fidelity PCR kit (New England Biolabs, F-553L) and pJ201: 25893 as template with combinations of the primers GCSF cyto-forward, GCSF cyto-reverse for cytoplasmic Met-GCSF construct; GCSF-peri-forward and GCSF cyto-reverse for the periplasmic constructs (Table 4). The PCR products were SapI digested and cloned into the rapid cloning vectors. Insert and vectors were ligated overnight with T4 DNA ligase (New England Biolabs, M0202S), and electroporated into competent *P. fluorescens* DC454 cells and transformants were selected on M9 glucose agar plates. Positive clones were selected and sequence-confirmed on both strands using primers in Table 2. The resulting cytoplasmic expression plasmid was named p529-013, which was transformed into 16 selected *P. fluorescens* host strains in 96-well format.

TABLE 4

Primers used in current study

| Name | Length | Oligo Sequence | SEQ ID NO: |
|---|---|---|---|
| GCSF-peri_forward | 34 | ATATGCTCTTCAGCCATGACTCCTCTGGGTCCTG | 1 |
| GCSF Cyto-reverse | 37 | ATATGCTCTTCTGAAGTGACTCTCGAGCTATTATCAC | 2 |
| GCSF Cyto-forward | 31 | ATATGCTCTTCAATGACTCCTCTGGGTCCTG | 3 |
| GCSF-Mid-forward | 19 | GCAGGCCTTGGAAGGCATC | 4 |
| GCSF-Mid_reverse | 19 | GATGCCTTCCAAGGCCTGC | 5 |
| Term | 18 | GCTGCCGCACAGCTCCAT | 6 |
| Ptac | 22 | CCGATGATCGGTAAATACCGAT | 7 |

DNA Sequencing

Clones were analyzed by sequencing using BigDye® Terminator v3.1 Cycle Sequencing Kit (Applied Biosystems, 4337455). Vector primers flanking the DNA insert and 2 insert specific primers (Table 4) were used to confirm the both strands of DNA from promoter through transcriptional terminator. Reactions consisted of 2 µL of sequencing premix, 1 µL of 6.4 µM primer, 50 fmol of DNA template, 3 µL 5× buffer, and H$_2$O to adjust volume to 20 µL. Sequencing reactions were purified using Sephadex G-50 (Sigma, 55897) and loaded into the ABI3100 sequencer. Sequence data were assembled and analyzed using Sequencher software (Gene Codes).

Growth and Expression in 96-Well Format

The effect of a variety of expression plasmids and host strains on Met-G-CSF expression was evaluated at the 96-well scale. Nineteen secretion leaders fused to Met-G-CSF constructs were tested in *P. fluorescens* DC454.

Cells were electroporated with indicated plasmids, resuspended in HTP growth medium with trace minerals and 5% glycerol and then transferred to 96-well deep well plates with 400 µM9 salts 1% glucose medium and trace elements. The 96-well plates were incubated at 30° C. with shaking for 48 hours. Ten microliters of these seed cultures were transferred into triplicate 96-well deep well plates, each well containing 500 µl of HTP medium, supplemented with trace elements and 5% glycerol, and incubated as before for 24 hours. Isopropyl βD 1 thiogalactopyranoside (IPTG) was added to each well for a final concentration of 0.3 mM to induce the expression of GCSF and temperature was reduced to 25° C. Twenty four hours after induction, cells were normalized to OD600=15 using PBS in a volume of 400 µl using the Biomek liquid handling station (Beckman Coulter). Samples were frozen for later processing by sonication and centrifugation to generate soluble and insoluble fractions.

Sample Preparation

Soluble fractions were prepared by sonication followed by centrifugation. Normalized culture broth samples (400 µL) were sonicated with the Cell Lysis Automated Sonication System (CLASS, Scinomix) with a 24 probe tip horn. The lysates were centrifuged at 14,000×rpm for 20 minutes (4° C.) and the supernatants collected (soluble fraction). Further dilutions of soluble samples for biolayer interferometry analysis were performed in ForteBio's Sample Diluent (PN, described below).

GCSF Binding Biolayer Interferometry

The lyophilized recombinant human granulocyte colony stimulating factor receptor (GCSF-R) (R & D Systems, cat# 381GR/CF) was reconstituted in PBS buffer (Sigma, P3813) to 0.5 mg/mL and biotinylated using NHS-LC-LC-biotin (Pierce, 21343) according to the method described in ForteBio Technical Note: "Biotinylation of Protein for Immobilization onto Streptavidin Sensors." The biosensors (Streptavidin High Binding FA Biosensors, ForteBio, 18-0009) were hydrated in 1× kinetics buffer (10-fold dilution of 10× Kinetics Buffer, ForteBio, 18-5032 into PBS) for at least 10 minutes. The sensors were loaded with 10 µg/mL biotinylated GCSF-R (b-GCSF-R) diluted into sample diluent (ForteBio, 18-1000) for at least 2 hours at room temperature or overnight at 4° C.

The soluble fraction of the strain array samples were diluted 20-fold into 1× kinetics buffer. Standards were diluted into *P. fluorescens* DC432 null soluble fraction. Samples and standards were loaded at a volume of 100 µL into half area plates (E&K Scientific, EK-78076). The b-GCSF-R loaded sensors were soaked in 1× kinetics buffer for ~5 minutes to rinse away unbound ligand, and then pre-equilibrated for 40-60 minutes in a dilution of null soluble fraction. The sample plate was pre-warmed at 30° C. in the Octet instrument for 10 minutes prior to initiating the assay. The samples were read at 200 rpm, 30° C., for 120 sec, and quantitation was calculated from a standard curve at 12, 6, 3, 1.5, 0.75, 0.375, 0.188, and in some cases as low as 0.094 µg/ml.

Intact Mass Analysis of Target Protein

For HTP samples, 50 µl soluble lysates were mixed with 50 µl of 5.4 M Gu-HCl, 100 mM DTT and heated at 37° C. for 10 min. The mixture was centrifuged at 18,000 g for 5 min. at room temperature (R.T.), and transferred to an autosample vial with a 200 µl polypropylene insert (Agilent, 5182-0549).

For mini-bioreactor (MBR) samples, ~75 µl of MBR lysates were subjected to acetone precipitation. Briefly, 6 volumes of cold acetone were added to the MBR lysates, vortexed and incubated on ice for 20 min. The mixtures were then centrifuging at 18,000 g for 5 min. at R.T. The pellets were washed with cold 85% acetone and centrifuged as above, and the pellets were air-dried for 10 min. The pellets were then solubilized in 50 µl of 5.4 M Gu-HCl, 100 mM DTT and heated at 37° C. for 10 min. Fifty µl of H$_2$O was added to each sample, the mixture was centrifuged as above, and supernatant was transferred to autosample vials.

The above HTP or MBR lysates were subjected to LC-MS analysis using an interconnected autosampler, column heater, UV detector, and HPLC (Agilent 1100) coupled to a Q-T of micro mass spectrometer (Waters) with an electrospray interface. A C8 column (Zorbax 5 um, 300SB-C8, 2.1×150 mm, Agilent) fitted with a guard column (Zorbax 5 um, 300SB-C8, 2.1×12.5 mm, Agilent) was used for separation. The HPLC buffers used were buffer A (0.1% formic acid) and buffer B (90% acetonitrile 0.1% formic acid). After the column was equilibrated at 5% buffer B and the sample was loaded, the on-column sample was subjected to one of two different reversed phase gradients. For the "70 min. C8 method," the column was washed at 5% B for 10 min., and then a 40 min. gradient from 5% to 60% B was used. For the "35 min. C8 method," after loading at 5% B, a steep linear gradient wa developed to 53% B over 10 min. Subsequently, a shallow gradient from 53% to 63% over 10 min. was developed. For both methods, after the gradient, the solvent was brought to 100% B for 5 min., ending with 5% B for 5 min. The retention time of G-CSF was ~51.5 min. and ~19.5 min. for the "70 min. C8 method" and the "35 min. C8 method," respectively.

Another column was used and method developed in hopes of reducing the clogging/fouling observed from the analysis of MBR lysates. A CN column (Zorbax 5 um, 300SB-CN, 2.1×150 mm, Agilent) fitted with a C3 guard column (Zorbax 5 um, 300SB-C3, 2.1×12.5 mm, Agilent) was used for separation. A LC method was developed for loading of lysates at 20% B, followed by a gradient of 20% to 40% B over 10 min., and followed by another gradient of 40% to 60% B over 20 min. The column was then brought to 100% B for 5 min., and ended with 20% B for 5 min. The retention time of G-CSF for this "40 min. CN method" is ~19.5 min.

UV absorbance was collected from 180-500 nm, prior to MS. The MS source was used in positive mode at 2.5 kV. MS scans were carried out using a range of 400-2400 m/z at 2 scans per second. MS and UV data were analyzed using MassLynx software (Waters). UV chromatograms of MS total ion current (TIC) chromatograms were generated. The MS spectra of the target peaks were summed. These spectra were deconvoluted using MaxEnt 1 (Waters) scanning for a molecular weight range of 14,000-24,000 at a resolution of 0.5 Da per channel.

Construction of G-CSF Expression Strains

Figure 3:
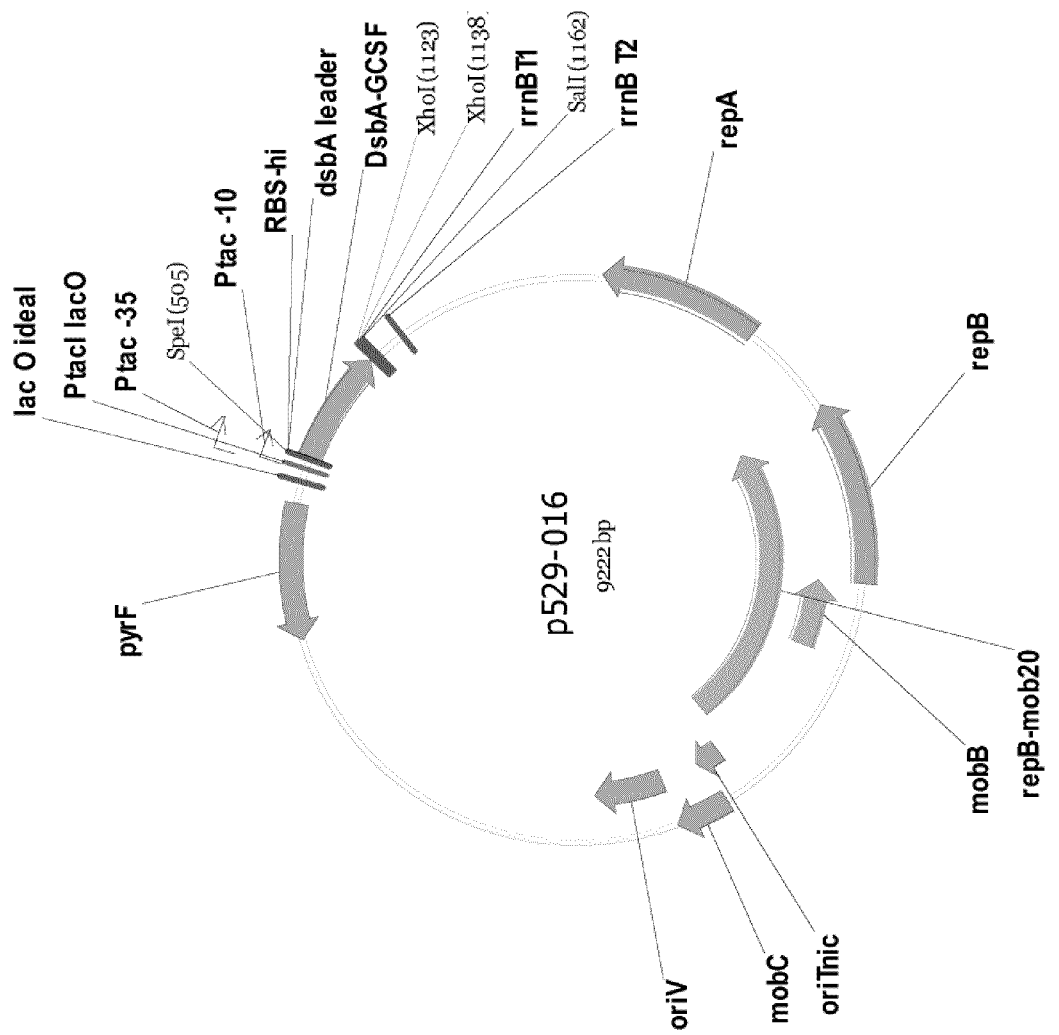
FIG. 3 depicts a representative expression plasmid map for a plasmid containing a G-CSF gene for expression in *P. fluorescens*. Plasmid p529-016 encodes G-CSF with Dsba secretion signal. Open reading frames are indicated by arrows, including the pyrF selectable marker. The relevant promoter and transcriptional terminator elements are also annotated.

An optimized human gcsf gene was designed and synthesized for expression in *P. fluorescens* as described above. Plasmids were constructed carrying the optimized gcsf gene fused to 19 different *P. fluorescens* secretion leaders (Retallack et al., 2007) (Table 5). The secretion leaders target the protein to the periplasm where it may be recovered in the properly folded and active form. The gene was cloned into the expression vectors as described, and the sequences were confirmed from the promoter through the transcriptional terminator. A representative plasmid map (p529-016) is shown in FIG. 3. Expression of the G-CSF was driven from the Ptac promoter, and translation initiated from a high activity ribosome binding site (RBS). The resulting 19 plasmids were transformed into *P. fluorescens* host strains as described below. Folding modulators, when present, were encoded on a second plasmid and expression driven by a mannitol inducible promoter.

TABLE 5

Secretion leaders tested for the Met-G-CSF construct

| Leader | Sequence | SEQ ID NO: |
|---|---|---|
| Pbp | MKLKRLMAAMTFVAAGVATVNAVA | 8 |
| DsbA | MRNLILSAALVTASLFGMTAQA | 9 |
| Azu | MFAKLVAVSLLTLASGQLLA | 10 |
| LAO | MQNYKKFLLAAAVSMAFSATAMA | 11 |
| Ibp-S31A | MIRDNRLKTSLLRGLTLTLLSLTLLSPAAHA | 12 |
| TolB | MRNLLRGMLVVICCMAGIAAA | 13 |
| Tpr | MNRSSALLLAFVFLSGCQAMA | 14 |
| Ttg2C | MQNRTVEIGVGLFLLAGILALLLLALRVSGLSA | 15 |
| FlgI | MKFKQLMAMALLLALSAVAQA | 16 |
| CupC2 | MPPRSIAACLGLLGLLMATQAAA | 17 |
| CupB2 | MLFRTLLASLTFAVIAGLPSTAHA | 18 |
| CupA2 | MSCTRAFKPLLLIGLATLMCSHAFA | 19 |
| NikA | MRLAALPLLLAPLFIAPMAVA | 20 |
| CopA | MSHFDLGRRRVMQAVGAGLLLPGLAPAVIA | 21 |
| Pbp-A20V | MKLKRLMAAMTFVAAGVATVNAVA | 22 |
| DsbC | MRLTQIIAAAAIALVSTFALA | 23 |
| Bce | MSTRIPRRQWLKGASGLLAAASLGRLANREARA | 24 |
| MdoD | MHRRNLLKASMAIAAYTGLSASGLLAAQAWA | 25 |
| OprF | MKLKNTLGLAIGSLIAATSFGVLA | 26 |

Small Scale Expression of G-CSF in *P. fluorescens*

The effect of a variety of expression plasmids and host strains on Met G-CSF expression was evaluated. No soluble Met G-CSF was detected from strains carrying the cytoplasmic construct p529-013, as determined by BLI. Soluble periplasmic expression, up to 250 mg/L, was detected in strains carrying a variety of secretion leader constructs (FIG. 1).

Soluble G-CSF expression up to 250 mg/L was detected in strains carrying a variety of secretion leader constructs (FIG. 1). For selected higher expression strains, Western blot and/or intact mass analysis were performed for target identification and evaluation of leader processing. The results indicated seven secretion leaders (Pbp, FlgI, DsbA, LAO, CupA2, Ibp and Pbp-A20V) were efficiently processed (data not shown).

Western blot and intact mass (data not shown) analysis were performed on selected strains. The results indicated six secretion leaders: Pbp, FlgI, DsbA, LAO, CupA2, and Ibp, were efficiently processed. Another leader, Pbp-A20V, was efficiently processed as determined by intact mass analysis (data not shown).

TABLE 6

Met-G-CSF Expression Strains.

| Signal Sequence | Plasmid No. |
|---|---|
| Pbp | p529-015 |
| DsbA | p529-016 |
| Lao | p529-017 |
| Ibp-S31A | p529-018 |
| FlgI | p529-019 |
| CupA2 | p529-020 |
| Pbp-A20V | p529-021 |

Screening of the Protease Deletions

All available protease deletion hosts of *P. fluorescens* were screened for minimal des-Met G-CSF production. Plasmids carrying Met-G-CSF gene fused to the secretion leaders (Table 6) were transformed into the protease deletion library. The resulting strains were grown for 24 hours, induced with IPTG and harvested 24 hours post induction.

TABLE 7

Selected plasmids for screening the protease deletion host library.

| Plasmid | Signal Sequence |
|---|---|
| p529-017 | Lao |
| p529-018 | Ibp-S31A |
| p529-020 | cupA2 |

Analysis of Protein Quantity and Quality

After harvest, samples were normalized to OD600 of 15. Cells were sonicated and separated into soluble and insoluble fractions. The soluble protein expression was analyzed by BLI binding to the GCSF-R. The soluble G-CSF yield ranged from non-detectable to 470 mg/L. The high G-CSF expressing strains were selected for quality evaluation by intact mass analysis. Table 8 shows the selected G-CSF expression strains and their corresponding LC-MS analysis. The des-Met (%) is the percentage of des-Met relative to the intact Met-G-CSF amount. The host strain MID4697, which contains an insertionally inactivated prtB gene, was identified as having the lowest level of des-Met GCSF.

TABLE 8

Top G-CSF Expression Strains Analyzed by LC-MS.

| Strain | Host | Plasmid | Yield (mg/L) | des-Met(%) |
|---|---|---|---|---|
| CS529-568 | MID4697 | p529-017 | 247 | 0.10 |
| CS529-648 | MID4697 | p529-020 | 297 | 0.30 |
| CS529-700 | DC0859 | p529-017 | 173 | 0.50 |
| CS529-750 | DC469 | p529-017 | 380 | 0.50 |
| CS529-708 | DC1020 | p529-017 | 281 | 1.00 |
| CS529-726 | DC1068 | p529-017 | 204 | 1.40 |
| CS529-709 | DC1021 | p529-017 | 146 | 1.60 |
| CS529-830 | DC469 | p529-020 | 321 | 1.70 |
| CS529-518 | DC518 | p529-017 | 335 | 2.70 |
| CS529-790 | DC1023 | p529-020 | 39 | 3.00 |
| CS529-705 | DC0977 | p529-017 | 191 | 3.20 |
| CS529-775 | DC1097 | p529-017 | 189 | 5.00 |
| CS529-707 | DC1011 | p529-017 | 193 | 5.00 |
| CS529-735 | DC1065 | p529-017 | 229 | 5.00 |
| CS529-731 | DC1084 | p529-017 | 233 | 5.00 |
| CS529-765 | MID4720 | p529-017 | 281 | 5.00 |
| CS529-563 | MID4692 | p529-017 | 302 | 5.00 |
| CS529-770 | MID4739 | p529-017 | 309 | 5.00 |
| CS529-828 | DC1067 | p529-020 | 336 | 5.00 |
| CS529-716 | DC1030 | p529-017 | 353 | 5.00 |
| CS529-564 | MID4693 | p529-017 | 354 | 5.00 |
| CS529-753 | DC487 | p529-017 | 425 | 5.00 |
| CS529-515 | DC508 | p529-017 | 430 | 5.00 |
| CS529-747 | DC1063 | p529-017 | 437 | 5.00 |
| CS529-829 | DC1076 | p529-020 | 457 | 5.00 |
| CS529-715 | DC1029 | p529-017 | 474 | 5.00 |
| CS529-818 | DC1074 | p529-020 | 545 | 5.00 |
| CS529-776 | DC1098 | p529-017 | 227 | 5.40 |
| CS529-571 | MID4707 | p529-017 | 299 | 6.00 |
| CS529-780 | DC0859 | p529-020 | 51 | 10.00 |
| CS529-806 | DC1068 | p529-020 | 82 | 10.00 |
| CS529-788 | DC1020 | p529-020 | 129 | 10.00 |
| CS529-789 | DC1021 | p529-020 | 146 | 10.00 |
| CS529-745 | DC954 | p529-017 | 250 | 10.00 |
| CS529-785 | DC0977 | p529-020 | 258 | 10.00 |
| CS529-556 | MID4764 | p529-017 | 274 | 10.00 |
| CS529-711 | DC1025 | p529-017 | 286 | 10.00 |
| CS529-782 | DC0955 | p529-020 | 302 | 10.00 |
| CS529-751 | DC485 | p529-017 | 304 | 10.00 |
| CS529-561 | MID4690 | p529-017 | 316 | 10.00 |
| CS529-762 | MID4717 | p529-017 | 366 | 10.00 |
| CS529-574 | MID4710 | p529-017 | 383 | 10.00 |
| CS529-756 | DC490 | p529-017 | 402 | 10.00 |
| CS529-796 | DC1030 | p529-020 | 409 | 10.00 |
| CS529-744 | DC441 | p529-017 | 414 | 10.00 |
| CS529-526 | DC987 | p529-017 | 418 | 10.00 |
| CS529-565 | MID4694 | p529-017 | 433 | 10.00 |
| CS529-820 | DC674 | p529-020 | 580 | 10.00 |
| CS529-703 | DC0956 | p529-017 | 208 | 15.00 |
| CS529-783 | DC0956 | p529-020 | 255 | 15.00 |
| CS529-853 | DC1095 | p529-020 | 312 | 15.00 |
| CS529-560 | MID4689 | p529-017 | 355 | 15.00 |
| CS529-519 | DC520 | p529-017 | 377 | 15.00 |
| CS529-544 | MID4749 | p529-017 | 383 | 15.00 |
| CS529-543 | MID2078 | p529-017 | 397 | 15.00 |
| CS529-541 | MID2074 | p529-017 | 449 | 15.00 |
| CS529-850 | MID4739 | p529-020 | 255 | 20.00 |
| CS529-554 | MID4761 | p529-017 | 319 | 20.00 |
| CS529-534 | DC1041 | p529-017 | 331 | 20.00 |
| CS529-517 | DC511 | p529-017 | 353 | 20.00 |
| CS529-545 | MID4750 | p529-017 | 358 | 20.00 |
| CS529-535 | DC1042 | p529-017 | 359 | 20.00 |
| CS529-514 | DC507 | p529-017 | 374 | 20.00 |
| CS529-525 | DC983 | p529-017 | 379 | 20.00 |
| CS529-712 | DC1026 | p529-017 | 350 | 25.00 |
| CS529-786 | DC1010 | p529-020 | 196 | 30.00 |
| CS529-840 | DC977 | p529-020 | 242 | 30.00 |
| CS529-546 | MID4751 | p529-017 | 336 | 30.00 |
| CS529-558 | MID4687 | p529-017 | 348 | 30.00 |
| CS529-834 | DC488 | p529-020 | 372 | 35.00 |
| CS529-718 | DC1033 | p529-017 | 164 | 40.00 |
| CS529-659 | DC696 | p529-020 | 192 | 45.00 |
| CS529-598 | DC518 | p529-020 | 175 | 50.00 |
| CS529-717 | DC1032 | p529-017 | 151 | 80.00 |
| CS529-719 | DC1034 | p529-017 | 132 | 100.00 |

Construction of a Clean Knock Out of prtB Gene

The host MID4697 showed only up to 0.3% des-Met G-CSF product from the cell lysates at the 96-well plate scale (Table 8). Strain MID4697 contains an insertional mutation of rxf08627, which encodes the extracellular serine protease PrtB, in a ΔaprA *P. fluorescens* strain. Strain MID4697 contains an antibiotic (kanamycin) resistant marker in its genome, which is not desirable. Therefore, an rxf08627 deletion strain was constructed.

A complete rxf08627 gene deletion strain was constructed to inactivate the annotated extracellular protease Rxf08627 from the genome. A deletion plasmid pDOW6800 was constructed by PCR amplification of two DNA fragments flanking the rxf08627 region. The two fragments were subsequently fused using the splicing by overlap extension PCR method. The fused DNA fragments were then ligated into the SrfI site of vector pDOW1261 to create the deletion plasmid pDOW6800. The insert of the deletion plasmid was confirmed by DNA sequencing. The deletion of rxf08627 gene was created by cross-in cross-out allele exchange as described (Schneider, et al., 2005). A clean deletion of rxf08627 was constructed in the wild type and ΔaprA *P. fluorescens* strain backgrounds, resulting in strains MID5093 and MID5103 respectively.

TABLE 9

New Strains Constructed for Expression of Met-G-CSF

| Strain Name | Signal Sequence | Plasmid | Host |
|---|---|---|---|
| CS529-900 | pbp | p529-015 | MID5093 |
| CS529-901 | dsbA | p529-016 | MID5093 |
| CS529-902 | Lao | p529-017 | MID5093 |
| CS529-903 | Ibp-S31A | p529-018 | MID5093 |
| CS529-904 | FlgI | p529-019 | MID5093 |
| CS529-905 | cupA2 | p529-020 | MID5093 |
| CS529-906 | Pbp-A20V | p529-021 | MID5093 |
| CS529-907 | pbp | p529-015 | MID5103 |
| CS529-908 | dsbA | p529-016 | MID5103 |
| CS529-909 | Lao | p529-017 | MID5103 |
| CS529-910 | Ibp-S31A | p529-018 | MID5103 |
| CS529-911 | FlgI | p529-019 | MID5103 |
| CS529-912 | cupA2 | p529-020 | MID5103 |
| CS529-913 | Pbp-A20V | p529-021 | MID5103 |

Strain Evaluation in Minibioreactors (MBR)

The expression strains were evaluated for production of soluble G-CSF in 9 different fermentation conditions using the µ-24™ micro-bioreactor (MBR; Applikon Biotechnology), a 24-well mini-bioreactor system designed to independently monitor and control pH, temperature and DO in each well. Fractional factorial DOE experiments were conducted to examine effects of varying multiple fermentation parameters. The MBR single-use polystyrene cassette had 24 wells and operated at a 4-mL working volume. For experiments conducted with oxygen as the sparging gas, the set points were programmed to maintain constant agitation, temperature and pH during the growth phase, and DO control was set at 30%. Glycerol was provided at 30-60 g/L in a minimal salts medium (Riesenberg et al., 1991) in order to support growth of the cultures to different induction ODs without the need for subsequent feed addition.

Production of recombinant Met G-CSF protein in *Pseudomonas fluorescens* Pfenex Expression Technology™ strain CS529-901 was successfully achieved in 2 liter fermentors. Multiple fermentation conditions were evaluated resulting in expression of Met G-CSF up to 0.35 g/L as measured by BLI binding assay.

Fermentation cultures were grown in 2 liter fermentors containing a mineral salts medium (Riesenberg, et al., 1991). Culture conditions were maintained at 32° C. and pH 6.5 through the addition of aqueous ammonia. Dissolved oxygen was maintained in excess through increases in agitation and flow of sparged air and oxygen into the fermentor. Glycerol was delivered to the culture throughout the fermentation to maintain excess levels. These conditions were maintained until the target culture optical density ($A_{575}$) for induction was reached, at which time IPTG was added to initiate Met G-CSF production. The optical density at induction, the concentration of IPTG, pH and temperature were all varied to determine optimal conditions for expression. After 16 hours, the culture from each fermentor was harvested by centrifugation and the cell pellet frozen at −80° C.

Figure 4:
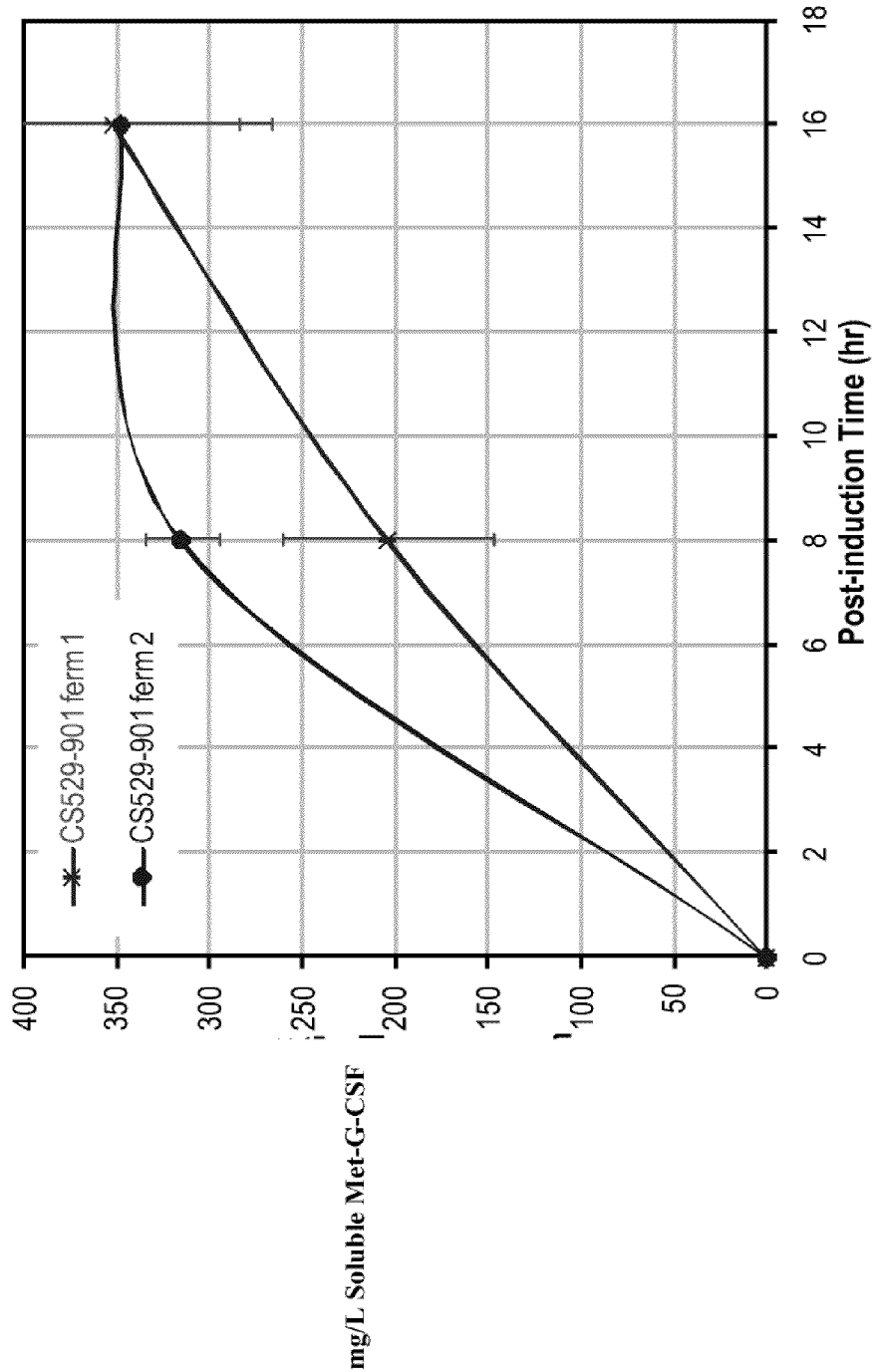
FIG. 4 depicts soluble Met G-CSF production for replicate fermentations of strain CS529-901. Replicate fermentations resulted in consistent Met G-CSF production at 0.35 g/L as determined by BLI binding assay, with time post induction shown on the X-axis and yield of active protein shown on the Y-axis. Error bars indicate standard deivation from 3 replicate samples for each time point.
Figure 5:
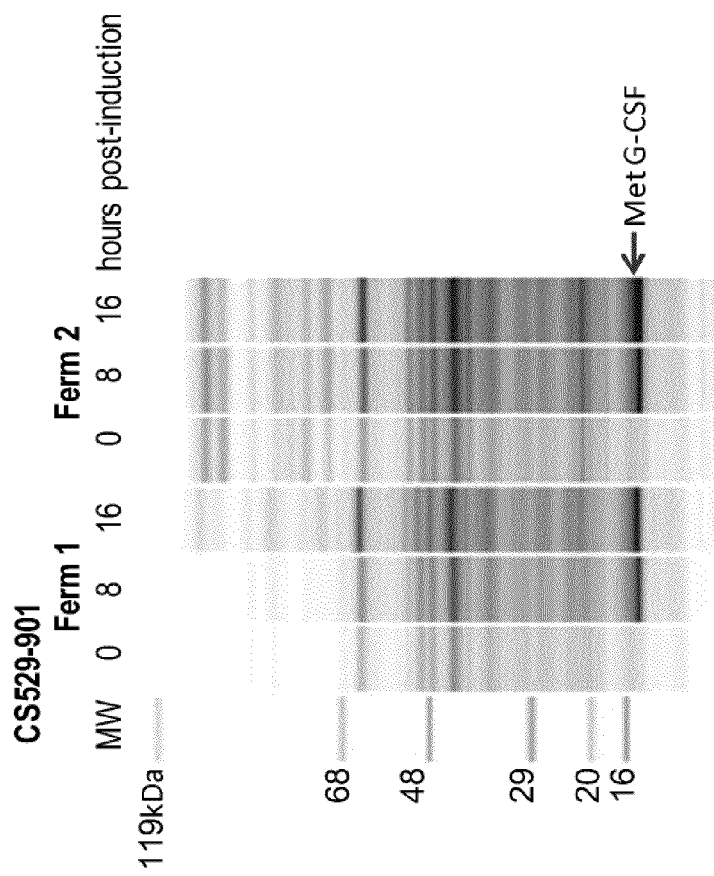
FIG. 5 depicts a gel-like image of soluble Met G-CSF production in replicate fermentations of strain CS529-901. Time post-induction for each fermentation is indicated above each lane. The migration of induced recombinant protein is indicated by the red arrow.

The exemplifying fermentation cultures, induced at 80 OD with 0.24 mM IPTG, pH and temperature setpoints adjusted to 6.0 of 28.5° C., respectively, resulted in 0.35 g/L of soluble, active Met G-CSF (FIGS. 4 and 5).

Evaluation of G-CSF Production in prtB Deletion Host Strains

Figure 2:
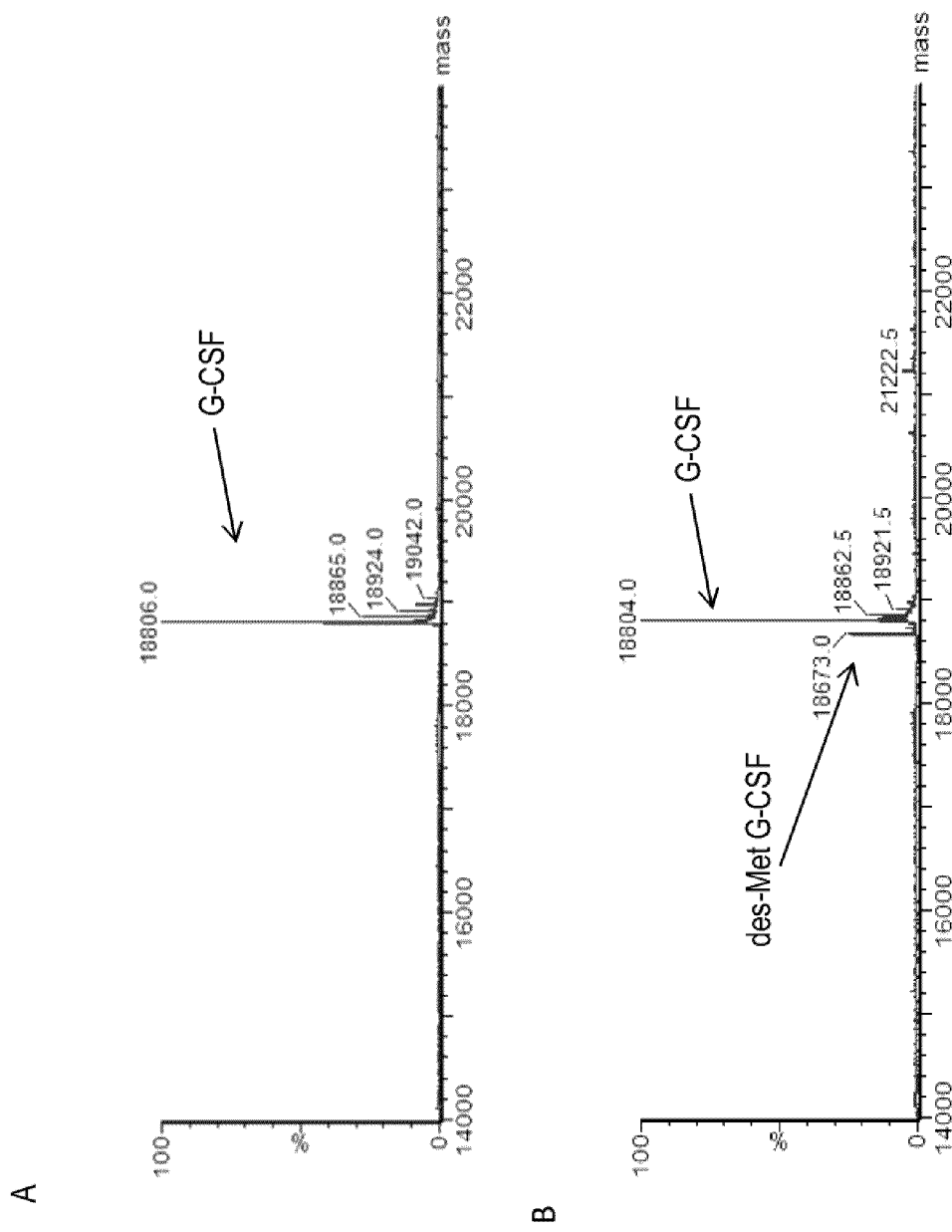
FIG. 2 illustrates intact mass analysis of target protein produced from representative strains following expression in minibioreactor cultures. The deconvoluted intact mass of the main peak corresponds to the intact Met-G-CSF at 18.80 kDa from CS529-901(A). Strain CS529-712 also produced a minor peak representing the des-Met product at 18.67 kDa (B).

The quality of the product from the newly constructed strains (clean deletion of prtB) (Table 9) was evaluated by LC-MS analysis following expression at the 4 mL fermentation scale; Met-GCSF was detected, while no des-Met G-CSF product was observed. FIG. 2 shows representative strains analyzed by LC-MS.

G-CSF In Vitro Cell Proliferative Activity Assay

Figure 8:
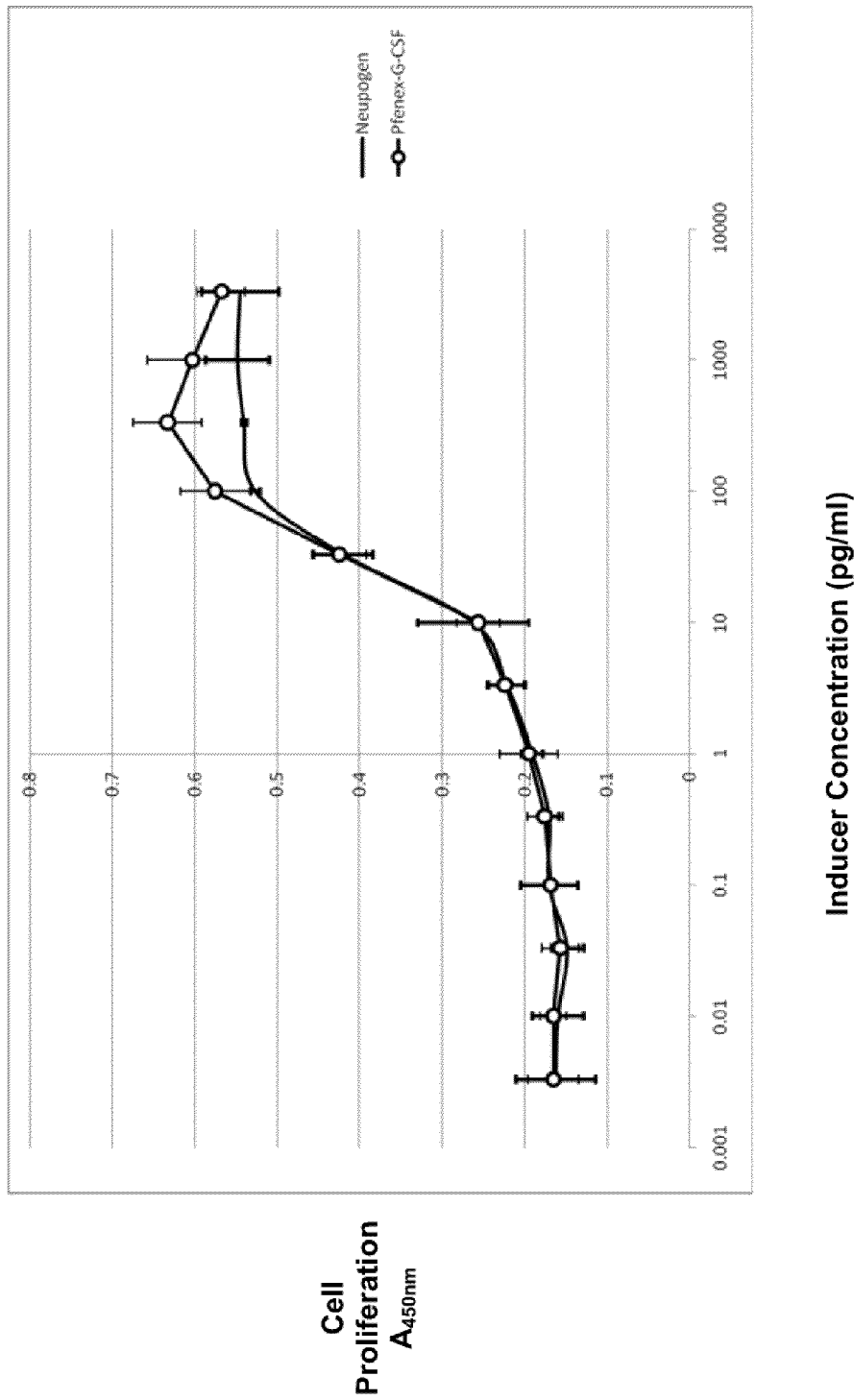
FIG. 8 shows the activity of *P. fluorescens*-produced G-CSF as indicated by proliferation of the murine myeloblastic cell line NFS-60. The concentration of CS5329-901-produced G-CSF (open circles) and Neupogen® (closed squares) in pg/ml is shown on the X-axis, and the absorbance at 450 nm representing cell proliferation is shown on the Y-axis. The error bars represent the standard error of three replicates for each point.

A G-CSF activity assay was performed using the myeloid leukemia M-NFS-60 proliferation method following the protocol described by Hammerling et al. (1995). The M-NFS-60 cell line was purchased from the American Type Culture Collection (ATCC, CRL-1838). The stimulatory effect of G-CSF was measured and compared with that of Neupogen® using a colorimetric assay utilizing a rapid cell proliferation assay kit (Calbiochem, QIA127). The purified Met-G-CSF induced NFS-60 cell proliferation, with a 50% Effective Dose (ED50) of 35 pg/mL. The dose responsive curve of purified G-CSF was very similar to that of Neupogen® in the M-NFS-60 proliferation assay (FIG. 8). As illustrated in FIG. 8, proliferation of the murine myeloblastic cell line NFS-60 was measured. The concentration of CS5329-901-produced G-CSF (open circles) and Neupogen® (closed squares) is shown on the X-axis, and the absorbance at 450 nm representing cell proliferation is shown on the Y-axis. The error bars represent the standard error of three replicates for each point.

REFERENCES

Covalt, J. C., Jr., Cao, T. B., Magdaroag, J. R., Gross, L. A. & Jennings, P. A. (2005). Temperature, media, and point of induction affect the N-terminal processing of interleukin-1beta. *Protein Expr Purif* 41, 45-52.

U. Hammerling, R. Kroon, and L. Sjodin, In vitro bioassay with enhanced sensitivity for human granulocyte colony-stimulating factor. J Pharm Biomed Anal. 13 (1995) 9-20.

Herman, A. C., Boone, T. C. & Lu, H. S. (1996). Characterization, formulation, and stability of Neupogen (Filgrastim), a recombinant human granulocyte-colony stimulating factor. *Pharm Biotechnol* 9, 303-28.

Okabe, M., Asano, M., Kuga, T., Komatsu, Y., Yamasaki, M., Yokoo, Y., Itoh, S., Morimoto, M. & Oka, T. (1990). In vitro and in vivo hematopoietic effect of mutant human granulocyte colony-stimulating factor. Blood 75, 1788-93.

Retallack, D. M., Schneider, J. C., Mitchell, J., Chew, L. & Liu, H. (2007). Transport of heterologous proteins to the periplasmic space of *Pseudomonas fluorescens* using a variety of native signal sequences. *Biotechnol Lett* 29, 1483-91.

Tanaka, H., Tanaka, Y., Shinagawa, K., Yamagishi, Y., Ohtaki, K. & Asano, K. (1997). Three types of recombinant human granulocyte colony-stimulating factor have equivalent biological activities in monkeys. *Cytokine* 9, 360-9.

Weston, B., Todd, R. F., 3rd, Axtell, R., Balazovich, K., Stewart, J., Locey, B. J., Mayo-Bond, L., Loos, P., Hutchinson, R. & Boxer, L. A. (1991). Severe congenital neutropenia: clinical effects and neutrophil function during treatment with granulocyte colony-stimulating factor. *J Lab Clin Med* 117, 282-90.

Riesenberg, D.; Schulz, V.; Knorre, W. A.; Pohl, H. D.; Korz, D.; Sanders, E. A.; Ross, A.; Deckwer, W. D. High cell density cultivation of *Escherichia coli* at controlled specific growth rate. *J. Biotechnol.* 1991, 20 (1), 17-27.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method comprising producing a soluble G-CSF protein in a *Pseudomonad* host cell, wherein at least 99% of the G-CSF protein comprises an N-terminal methionine, wherein the *Pseudomonad* host cell has a mutation in at least one gene encoding at least one protease, wherein the mutation results in the inactivation of the at least one protease, and wherein the at least one protease inactivated is PrtB; both PrtB and AprA; both the serine peptidase encoded by SEQ ID NO: 29 and the S41 protease encoded by SEQ ID NO: 30; an HtpX protease encoded by SEQ ID NO: 31; or both the serine peptidase encoded by SEQ ID NO: 29 and the Lon protease encoded by SEQ ID NO: 32.

2. The method of claim 1, wherein the producing comprises expressing the G-CSF protein from an expression construct.

3. The method of claim 2, wherein the expression construct is in a plasmid.

4. The method of claim 2, wherein the expression construct comprises a sequence encoding the G-CSF protein fused to a secretion leader.

5. The method of claim 4, wherein the secretion signal directs transfer of the G-CSF protein to the periplasm of the *Pseudomonad* host cell.

6. The method of claim 4, wherein the secretion signal is cleaved from the G-CSF protein in the *Pseudomonad* host cell.

7. The method of claim 4, wherein the secretion leader protein sequence comprises any one of SEQ ID NOs: 8-26.

8. The method of claim 1, wherein the mutation that results in the inactivation of the at least one protease is a complete deletion.

9. The method of claim 1, wherein the *Pseudomonad* host cell is a *Pseudomonas* host cell.

10. The method of claim 9, wherein the *Pseudomonas* host cell is a *Pseudomonas fluorescens* host cell.

11. The method of claim 1, wherein the G-CSF protein is human G-CSF protein.

12. The method of claim 1, further comprising determining the yield of the G-CSF protein, wherein the yield of the G-CSF protein is about 0.1 g/L to about 10 g/L.

13. The method of claim 1, further comprising determining the activity of the G-CSF protein.

14. The method of claim 13, wherein said activity is determined by binding recombinant G-CSF receptor.

15. A method comprising producing a soluble G-CSF protein in a *Pseudomonad* host cell, wherein at least 99% of the G-CSF protein comprises an N-terminal methionine, wherein refolding the Met-G-CSF protein is not required, and wherein the yield of soluble Met-G-CSF protein is about 0.1 g/L to about 10 g/L.

16. The method of claim 15, wherein the producing comprises expressing the G-CSF protein from an expression construct.

17. The method of claim 16, wherein the expression construct is a plasmid.

18. The method of claim 16, wherein the expression construct comprises a sequence encoding G-CSF protein fused to a secretion leader.

19. The method of claim 18, wherein the secretion leader directs transfer of the G-CSF protein to the periplasm of the *Pseudomonad* host cell.

20. The method of claim 18, wherein the secretion leader is cleaved from the G-CSF protein in the *Pseudomonad* host cell.

21. The method of claim 18, wherein the secretion leader comprises any one of SEQ ID NOs: 8-26.

22. The method of claim 15, wherein the *Pseudomonad* host cell is a *Pseudomonas* host cell.

23. The method of claim 22, wherein the *Pseudomonas* host cell is a *Pseudomonas fluorescens* host cell.

24. The method of claim 15, wherein the G-CSF protein is human G-CSF protein.

25. The method of claim 15, further comprising determining the activity of the G-CSF protein.

26. The method of claim 25, wherein the activity is determined by binding recombinant G-CSF receptor.

* * * * *

SEQUENCE LISTING

```
<160> NUMBER OF SEQ ID NOS: 34

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
atatgctctt cagccatgac tcctctgggt cctg                                  34

<210> SEQ ID NO 2
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
atatgctctt ctgaagtgac tctcgagcta ttatcac                               37

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atatgctctt caatgactcc tctgggtcct g                                     31

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gcaggccttg gaaggcatc                                                   19

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gatgccttcc aaggcctgc                                                   19
```

-continued

```
<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gctgccgcac agctccat                                                    18

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ccgatgatcg gtaaataccg at                                               22

<210> SEQ ID NO 8
<211> LENGTH: 24
<212> TYPE: PRT
<213> ORGANISM: Pseudomonas fluorescens

<400> SEQUENCE: 8

Met Lys Leu Lys Arg Leu Met Ala Ala Met Thr Phe Val Ala Ala Gly
1               5                   10                  15

Val Ala Thr Ala Asn Ala Val Ala
            20

<210> SEQ ID NO 9
<211> LENGTH: 22
<212> TYPE: PRT
<213> ORGANISM: Pseudomonas fluorescens

<400> SEQUENCE: 9

Met Arg Asn Leu Ile Leu Ser Ala Ala Leu Val Thr Ala Ser Leu Phe
1               5                   10                  15

Gly Met Thr Ala Gln Ala
            20

<210> SEQ ID NO 10
<211> LENGTH: 20
<212> TYPE: PRT
<213> ORGANISM: Pseudomonas fluorescens

<400> SEQUENCE: 10

Met Phe Ala Lys Leu Val Ala Val Ser Leu Leu Thr Leu Ala Ser Gly
1               5                   10                  15

Gln Leu Leu Ala
            20

<210> SEQ ID NO 11
<211> LENGTH: 23
<212> TYPE: PRT
<213> ORGANISM: Pseudomonas fluorescens

<400> SEQUENCE: 11

Met Gln Asn Tyr Lys Lys Phe Leu Leu Ala Ala Ala Val Ser Met Ala
1               5                   10                  15

Phe Ser Ala Thr Ala Met Ala
```

-continued

```
<210> SEQ ID NO 12
<211> LENGTH: 31
<212> TYPE: PRT
<213> ORGANISM: Pseudomonas fluorescens

<400> SEQUENCE: 12

Met Ile Arg Asp Asn Arg Leu Lys Thr Ser Leu Leu Arg Gly Leu Thr
1               5                   10                  15

Leu Thr Leu Leu Ser Leu Thr Leu Leu Ser Pro Ala Ala His Ala
            20                  25                  30

<210> SEQ ID NO 13
<211> LENGTH: 21
<212> TYPE: PRT
<213> ORGANISM: Pseudomonas fluorescens

<400> SEQUENCE: 13

Met Arg Asn Leu Leu Arg Gly Met Leu Val Val Ile Cys Cys Met Ala
1               5                   10                  15

Gly Ile Ala Ala Ala
            20

<210> SEQ ID NO 14
<211> LENGTH: 21
<212> TYPE: PRT
<213> ORGANISM: Pseudomonas fluorescens

<400> SEQUENCE: 14

Met Asn Arg Ser Ser Ala Leu Leu Ala Phe Val Phe Leu Ser Gly
1               5                   10                  15

Cys Gln Ala Met Ala
            20

<210> SEQ ID NO 15
<211> LENGTH: 33
<212> TYPE: PRT
<213> ORGANISM: Pseudomonas fluorescens

<400> SEQUENCE: 15

Met Gln Asn Arg Thr Val Glu Ile Gly Val Gly Leu Phe Leu Leu Ala
1               5                   10                  15

Gly Ile Leu Ala Leu Leu Leu Leu Ala Leu Arg Val Ser Gly Leu Ser
            20                  25                  30

Ala

<210> SEQ ID NO 16
<211> LENGTH: 21
<212> TYPE: PRT
<213> ORGANISM: Pseudomonas fluorescens

<400> SEQUENCE: 16

Met Lys Phe Lys Gln Leu Met Ala Met Ala Leu Leu Leu Ala Leu Ser
1               5                   10                  15

Ala Val Ala Gln Ala
            20

<210> SEQ ID NO 17
<211> LENGTH: 23
<212> TYPE: PRT
<213> ORGANISM: Pseudomonas fluorescens
```

```
<400> SEQUENCE: 17

Met Pro Pro Arg Ser Ile Ala Ala Cys Leu Gly Leu Leu Gly Leu Leu
1               5                   10                  15
Met Ala Thr Gln Ala Ala Ala
            20

<210> SEQ ID NO 18
<211> LENGTH: 24
<212> TYPE: PRT
<213> ORGANISM: Pseudomonas fluorescens

<400> SEQUENCE: 18

Met Leu Phe Arg Thr Leu Leu Ala Ser Leu Thr Phe Ala Val Ile Ala
1               5                   10                  15
Gly Leu Pro Ser Thr Ala His Ala
            20

<210> SEQ ID NO 19
<211> LENGTH: 25
<212> TYPE: PRT
<213> ORGANISM: Pseudomonas fluorescens

<400> SEQUENCE: 19

Met Ser Cys Thr Arg Ala Phe Lys Pro Leu Leu Leu Ile Gly Leu Ala
1               5                   10                  15
Thr Leu Met Cys Ser His Ala Phe Ala
            20                  25

<210> SEQ ID NO 20
<211> LENGTH: 21
<212> TYPE: PRT
<213> ORGANISM: Pseudomonas fluorescens

<400> SEQUENCE: 20

Met Arg Leu Ala Ala Leu Pro Leu Leu Leu Ala Pro Leu Phe Ile Ala
1               5                   10                  15
Pro Met Ala Val Ala
            20

<210> SEQ ID NO 21
<211> LENGTH: 30
<212> TYPE: PRT
<213> ORGANISM: Pseudomonas fluorescens

<400> SEQUENCE: 21

Met Ser His Phe Asp Leu Gly Arg Arg Arg Val Met Gln Ala Val Gly
1               5                   10                  15
Ala Gly Leu Leu Leu Pro Gly Leu Ala Pro Ala Val Ile Ala
            20                  25                  30

<210> SEQ ID NO 22
<211> LENGTH: 24
<212> TYPE: PRT
<213> ORGANISM: Pseudomonas fluorescens

<400> SEQUENCE: 22

Met Lys Leu Lys Arg Leu Met Ala Ala Met Thr Phe Val Ala Ala Gly
1               5                   10                  15
Val Ala Thr Val Asn Ala Val Ala
            20

<210> SEQ ID NO 23
```

<211> LENGTH: 21
<212> TYPE: PRT
<213> ORGANISM: Pseudomonas fluorescens

<400> SEQUENCE: 23

Met Arg Leu Thr Gln Ile Ile Ala Ala Ala Ile Ala Leu Val Ser
1               5                   10                  15

Thr Phe Ala Leu Ala
            20

<210> SEQ ID NO 24
<211> LENGTH: 33
<212> TYPE: PRT
<213> ORGANISM: Pseudomonas fluorescens

<400> SEQUENCE: 24

Met Ser Thr Arg Ile Pro Arg Arg Gln Trp Leu Lys Gly Ala Ser Gly
1               5                   10                  15

Leu Leu Ala Ala Ala Ser Leu Gly Arg Leu Ala Asn Arg Glu Ala Arg
            20                  25                  30

Ala

<210> SEQ ID NO 25
<211> LENGTH: 31
<212> TYPE: PRT
<213> ORGANISM: Pseudomonas fluorescens

<400> SEQUENCE: 25

Met His Arg Arg Asn Leu Leu Lys Ala Ser Met Ala Ile Ala Ala Tyr
1               5                   10                  15

Thr Gly Leu Ser Ala Ser Gly Leu Leu Ala Ala Gln Ala Trp Ala
            20                  25                  30

<210> SEQ ID NO 26
<211> LENGTH: 24
<212> TYPE: PRT
<213> ORGANISM: Pseudomonas fluorescens

<400> SEQUENCE: 26

Met Lys Leu Lys Asn Thr Leu Gly Leu Ala Ile Gly Ser Leu Ile Ala
1               5                   10                  15

Ala Thr Ser Phe Gly Val Leu Ala
            20

<210> SEQ ID NO 27
<211> LENGTH: 525
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(525)

<400> SEQUENCE: 27 atg act cct ctg ggt cct gca agt agt ctg ccg caa agt ttt ctc ctg     48
Met Thr Pro Leu Gly Pro Ala Ser Ser Leu Pro Gln Ser Phe Leu Leu
1               5                   10                  15 aag tgc ctg gaa cag gtg cgc aaa att cag ggc gac ggc gca gca ctg     96
Lys Cys Leu Glu Gln Val Arg Lys Ile Gln Gly Asp Gly Ala Ala Leu
            20                  25                  30 cag gaa aaa ctg tgc gcg acc tat aag ttg tgc cac ccc gaa gaa ctg    144
Gln Glu Lys Leu Cys Ala Thr Tyr Lys Leu Cys His Pro Glu Glu Leu

```
                35                  40                  45
gtg ctg ctg ggc cat agc ctg ggg att cca tgg gcg ccg ctg tcg tcc       192
Val Leu Leu Gly His Ser Leu Gly Ile Pro Trp Ala Pro Leu Ser Ser
 50                  55                  60 tgt cct agt caa gcc ttg caa ttg gcc ggt tgc ctc tcg caa ctg cat       240
Cys Pro Ser Gln Ala Leu Gln Leu Ala Gly Cys Leu Ser Gln Leu His
 65                  70                  75                  80 agc ggc ctg ttc ctg tac caa ggc ctg ctg cag gcc ttg gaa ggc atc       288
Ser Gly Leu Phe Leu Tyr Gln Gly Leu Leu Gln Ala Leu Glu Gly Ile
                 85                  90                  95 tcc ccg gaa ctg ggc ccg acg ctg gat acc ctg caa ctg gac gta gca       336
Ser Pro Glu Leu Gly Pro Thr Leu Asp Thr Leu Gln Leu Asp Val Ala
                100                 105                 110 gat ttc gcc acg acc atc tgg cag cag atg gaa gaa ctg ggc atg gcc       384
Asp Phe Ala Thr Thr Ile Trp Gln Gln Met Glu Glu Leu Gly Met Ala
            115                 120                 125 ccg gcc ctc cag ccc acg caa ggc gcg atg cct gca ttc gcc tcg gcg       432
Pro Ala Leu Gln Pro Thr Gln Gly Ala Met Pro Ala Phe Ala Ser Ala
        130                 135                 140 ttt caa cgc cgt gcg ggt ggc gtg ctg gta gcc agc cat ttg cag agc       480
Phe Gln Arg Arg Ala Gly Gly Val Leu Val Ala Ser His Leu Gln Ser
145                 150                 155                 160 ttt ctg gag gtg agc tat cgc gtc ctc cgt cat ctc gcc caa ccg           525
Phe Leu Glu Val Ser Tyr Arg Val Leu Arg His Leu Ala Gln Pro
                165                 170                 175

<210> SEQ ID NO 28
<211> LENGTH: 175
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Thr Pro Leu Gly Pro Ala Ser Ser Leu Pro Gln Ser Phe Leu Leu
 1               5                  10                  15

Lys Cys Leu Glu Gln Val Arg Lys Ile Gln Gly Asp Gly Ala Ala Leu
             20                  25                  30

Gln Glu Lys Leu Cys Ala Thr Tyr Lys Leu Cys His Pro Glu Glu Leu
         35                  40                  45

Val Leu Leu Gly His Ser Leu Gly Ile Pro Trp Ala Pro Leu Ser Ser
 50                  55                  60

Cys Pro Ser Gln Ala Leu Gln Leu Ala Gly Cys Leu Ser Gln Leu His
 65                  70                  75                  80

Ser Gly Leu Phe Leu Tyr Gln Gly Leu Leu Gln Ala Leu Glu Gly Ile
                 85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

<210> SEQ ID NO 29
```

```
<211> LENGTH: 1158
<212> TYPE: DNA
<213> ORGANISM: Pseudomonas fluorescens

<400> SEQUENCE: 29
atgctcaagg cactgcgttt ttttggatgg ccattgttgg ctggcgtgct gatcgcgatg      60
ctgattatcc agcgttatcc ccagtgggtg ggcctgccca cactggatgt gaacctgcaa     120
caggcgccgc agaccaacac ggtggtgcag ggcccggtga cctatgccga tgccgtggtc     180
attgccgcgc cggcggtggt caacctgtac accaccaagg tcatcaacaa gcccgcgcat     240
ccgttgtttg aagacccgca atttcgccgc tatttcggtg acaacggccc caagcagcgc     300
cgcatggaat ccagcctcgg ctccggtgtg atcatgagcc ccgagggcta catcctcacc     360
aacaaccacg tgaccaccgg cgccgaccag atcgtggtgg ccctgcgtga cggccgcgaa     420
accctggccc gcgtggtggg cagcgacccg gaaacggatc tggcggtact caagattgat     480
ctgaagaacc taccggccat caccctcggc cgctccgacg gtttgcgcgt gggcgatgtg     540
gcgctggcca tcggcaaccc gttcggggtg gccagacggt gaccatgggc atcatcagc     600 gccaccgggc gcaaccagct gggccttaac agctacgaag atttcatcca gaccgacgcg     660
gcgatcaacc ccggcaactc cggcggtgcg ctggtggacg ccaatggcaa cctgaccggc     720
atcaacaccg cgatttttc caagtccggc ggttcacagg cattgggtt tgcgatcccg      780 gtgaagctgg cgatggaagt gatgaagtcg atcatcgagc acggccaggt gattcgcggc     840
tggctgggca ttgaagtaca gcccttgacc aaggaactgg ccgaatcatt cggcctgacc     900
gggcgtccag gcatcgtggt agcggggatc ttccgcgacg gccggcgca gaaggccggc      960 ctgcaactgg gcgatgtgat cctcagcatc gacggcgccc cggcgggtga tggccgcaag    1020
tcgatgaacc aggtggctcg gatcaagccg accgacaagg tggcgatcct ggtgatgcgc    1080
aacggcaagg agatcaaact gtcggcggaa atcggcctgc cccaccacc ggcgaccgcg     1140 ccagtgaaag aagagcaa                                                  1158

<210> SEQ ID NO 30
<211> LENGTH: 2112
<212> TYPE: DNA
<213> ORGANISM: Pseudomonas fluorescens

<400> SEQUENCE: 30
atgcgttatc aattgcccccc gcgtcgaatc agcatgaagc atctgttccc cagcaccgcc     60
ctcgcttttt tcattggtct cggcttcgcg tcgatgtcga ccaatacgtt cgcagccaat    120
agctgggaca accttcagcc tgatcgcgat gaggtgattg ccagccttaa cgtcgtcgag    180
ttgcttaagc gccatcacta cagcaagccg ccgctggacg acgctcgctc agtgatcatc    240
tacgacagct acctcaagct gctggacccg tcgcgcagct acttcctggc cagcgatatc    300
gctgagttcg acaagtggaa gacgcaattc gacgacttcc tcaagagcgg cgacctgcag    360
cctggcttca ccatctacaa cgcgctacct gaccgcgtca agcgcgtct ggacttcgcc      420 ctgggtgagc tgaacaaagg cgtcgacaag ctcgatttca cccagaaaga aacccttctg    480
gtggaccgca aggacgcccc ttggctgacc agcaccgcag ccctagacga cctgtggcgc    540
aaacgcgtca aggacgaagt gctgcgcttg aagatcgccg gcaaagagcc caaggccatt    600
caagagctgt tgaccaagcg ctacaaaaac cagctggcgc gcctggacca gacccgtgcc    660
gaggatatct tccaggccta catcaacacc tttgcgatgt cctacgaccc gcacaccaat    720
tatctgtcgc cagataacgc ggaaaatttc gatatcaata tgagtctgtc cctggaaggc    780
```

-continued

| | |
|---|---|
| atcggtgccg tcctgcaaag cgacaatgac caggtgaaga ttgtacgtct ggtgccggca | 840 |
| ggcccggctg acaaaaccaa gcaagtggca ccggccgaca agatcatcgg cgtggcccag | 900 |
| gccgacaaag agatggtcga tgtggtcggc tggcgcctgg acgaagtggt caagctgatc | 960 |
| cgtgggccta aaggcagcgt ggtgcgcctg gaagtgattc cgcacaccaa tgcaccgaac | 1020 |
| gaccagacca gcaagatcgt gtccatcacc cgtgaagcgg tgaagctcga agaccaggcc | 1080 |
| gtgcagaaga agtcctcaa cctcaagcag gatggcaagg actacaagct gggggtgatt | 1140 |
| gaaatcccgg ccttctacct ggacttcaag gcgttccgtg ccggtgatcc ggactacaag | 1200 |
| tccaccaccc gcgacgtgaa gaaaatcctc acagaactgc agaaagagaa agtcgacggc | 1260 |
| gtggtcatcg acctgcgcaa caacggcggc ggctccctgc aggaagccac cgagctgacc | 1320 |
| agcctgttta cgacaaggg cccgaccgtg ttggtacgca acgctgacgg ccgtgtcgac | 1380 |
| gtgctcgaag acgagaaccc gggggccttc tacaaagggc cgatggcgct gctggtcaac | 1440 |
| cgcctctcgg cctcggcctc ggagattttc gccggtgcca tgcaggacta ccaccgtgca | 1500 |
| ctgatcatcg gcggccagac cttcggcaaa ggcaccgtgc agaccatcca gccgctgaac | 1560 |
| catggcgagc ttaagctgac actgccaag ttctaccggg tctccgggca gagcacccag | 1620 |
| catcagggcg tactgccgga tatcgatttc ccgtcgatca tcgacaccaa ggaaattggc | 1680 |
| gaaagcgccc tgcctgaagc catgccgtgg acaccatcc gccctgcgat caagccggcg | 1740 |
| tcggatccgt tcaagccgtt cctggcacag ctgaaggctg accacgacac ccgctctgcc | 1800 |
| aaggatgccg agttcgtgtt tatccgcgac aagctggccc tggccaagaa gctgatggaa | 1860 |
| gagaagaccg tcagcctcaa cgaagcggat cgccgtgcac agcactccag catcgagaat | 1920 |
| cagcaactgg tgctgaaaaa cacccgccgc aaggccaaag gtgaagaccc gctcaaagag | 1980 |
| ctgaagaaag aagatgaaga cgcgctgccg accgaggcgg ataaaaccaa gccggaagac | 2040 |
| gacgcctact tggccgagac tggccggatc ctgctggatt acctgaagat caccaagcag | 2100 |
| gtggccaagc ag | 2112 |

<210> SEQ ID NO 31
<211> LENGTH: 885
<212> TYPE: DNA
<213> ORGANISM: Pseudomonas fluorescens

<400> SEQUENCE: 31

| | |
|---|---|
| atgatgcgca tcctgctgtt cttggccact aacctggcgg tcgtactgat tgccagcgtc | 60 |
| accctgagcc ttttttggctt caacgggttc atggcggcca atggggttga tctgaacctc | 120 |
| aatcagctgc tgattttctg tgcggtcttt ggttttgccg gctcgctgtt ctcgctgttc | 180 |
| atctccaagt ggatggcgaa gatgagcacc agcacccaga tcatcactca accccgcact | 240 |
| cgccatgaac aatggctgat gcaaaccgtg gagcagttgt ctcaagaagc aggcatcaaa | 300 |
| atgcccgaag tggggatttt tcctgcttat gaggccaacg cctttgccac cggctggaac | 360 |
| aagaacgacg cactggtggc tgtgagccag ggcctgctgg agcggttttc gcccgatgaa | 420 |
| gtcaaggcgt gctggcccca cgagatcggc acgtagccaa acggcgacat ggtcaccctg | 480 |
| gcactggtac agggcgtggt gaacaccttc gtgatgttct ttgcgcggat catcggcaac | 540 |
| tttgtcgaca aggtcatctt caagaacgaa gaaggccgtg gcattgccta cttcgtggcg | 600 |
| accattttcg ccgagttggt cctgggcttc ctggccagcg ccatcgtgat gtggttctcg | 660 |
| cgcaaacgcg agttccgcgc agatgaagcc ggcgcacgcc tggcgggcac cagcgcaatg | 720 |
| atcggcgcgc tgcaacgcct gcgctccgaa cagggcctgc cggtgcatat gccggacagc | 780 |

```
ctgaccgcct tcggcatcaa cggcggcatc aagcagggcc tggctcgctt gttcatgagc    840
cacccgccgc tggaagagcg gattgacgca ctgcgtcgcc ggggc                    885
```

<210> SEQ ID NO 32
<211> LENGTH: 2394
<212> TYPE: DNA
<213> ORGANISM: Pseudomonas fluorescens

<400> SEQUENCE: 32

```
atgaagacaa ccatcgaatt gcctctcctg ccgttgcgtg atgtcgtcgt ctatccgcac      60
atggttatcc cgctgttcgt ggggcgcgag aagtctatcg aagccctcga ggccgcgatg    120
acgggcgaca agcaaatcct gctgttggcc cagaagaatc ctgctgatga tgatccgggc    180
gaagatgccc tgtatcgcgt cggcaccatt gccactgtcc tgcaattgct caagctgccc    240
gatggcaccg tcaaggtgct ggtcgaaggc gagcagcgcg gtgccgtaga gcgctttatg    300
gaggtggacg gccacctgcg cgcggaagtg gcactgatcg aagaagtcga agccccggag    360
cgtgaatccg aggtgttcgt gcgcagcctg ctgtcgcagt cgagcagta tgtgcagttg    420 ggcaagaaag tcccggctga agtcctgtcg tccctcaaca gcattgatga gccaagccgc    480
ctggtcgaca ccatggccgc gcacatggcg ctgaaaatcg agcagaagca agacatcctc    540
gaaatcatcg acctgtcggc ccgtgtcgaa cacgtactgg cgatgctgga tggcgaaatc    600
gacctgttgc aggttgaaaa acgcatccgt ggtcgcgtga aaaagcagat ggagcgtagc    660
cagcgcgagt actacctgaa tgagcagatg aaggccattc agaaggaact cggcgacggc    720
gaggaaggcc acaacgaaat cgaagagctg aaaaagcgca tcgatgccgc tggcctgccc    780
aaagacgccc tgaccaaggc caccgccgag ctgaacaagc tcaagcagat gtcgccgatg    840
tcggctgaag ccaccgtggt gcgctcgtat atcgactggc tggtgcaagt gccgtggaag    900
gcccagacca aggtgcgtct ggacctggcc cgtgctgaag agattctcga cgctgaccat    960
tacggcctgg aagaggtcaa ggagcgcatc cttgagtacc tcgctgtaca aaaacgcgtg   1020
aagaaaatcc gcggcccggt gttgtgcctg gttgggcctc cgggcgtggg taaaacctcc   1080
ctggcggaat caattgccag cgcgaccaac cgcaaattcg tgcgcatggc cttgggtggc   1140
gtgcgtgacg aagcggaaat cgcggtcat cgccgtacct acatcggttc gatgccggga   1200
agattgattc aaaagatgac aaaagtgggt gtacgcaacc cgctgttcct gctcgatgaa   1260
atcgacaaaa tgggcagcga catgcgtggc gacccggcgt cggctttgct cgaagtgctg   1320 gacccctgagc agaaccataa tttcaacgac cattacctgg aagtcgacta cgacttgtct   1380
gacgtaatgt tcctgtgcac ctccaactcc atgaacattc cgccagcctt gctggaccgg   1440
atggaggtga ttcgtctgcc gggctacacc gaagacgaga gatcaacat cgcggtcaag   1500 tacttggcgc ccaagcagat ttcggccaac ggcctgaaga agggcgagat cgaattcgag   1560
gtcgaggcga tccgcgacat cgtgcgctac tacactcgcg aggccggtgt gcggggcctt   1620
gagcgccaga tcgcgaagat ctgccgcaaa gcggtgaagg aacacgcgtt ggaaaaacgc   1680
ttctcggtga aagtggttgc cgactccctg gagcacttcc tgggcgtgaa gaaattccgc   1740
tacggcctgg ccgagcaaca ggaccaggtc ggccaggtga ctggcctggc gtggacccag   1800
gtgggtggcg aattgctcac catcgaagct gcggtgatte cgggcaaagg ccagttgatc   1860
aagaccggct ccctgggtga cgtgatggtc gaatccatta ccgccgcgca gaccgtggta   1920
cgcagccgcg cccgcagcct gggcatcccg ctggacttcc acgagaagca cgacacccat   1980
atccacatgc cggaaggggc gaccccaaa gacggccta gcgcgggcgt aggcatgtgc   2040
```

```
acggccctcg tgtcggcctt gaccggcatt cccgtgcgcg ccgatgtggc gatgaccggg    2100
gaaatcaccc tgcgtggcca ggtattggcg atcggtggtc tcaaagagaa attgctcgcc    2160
gcgcaccggg gtggaatcaa gactgtgatc attcctgaag agaatgttcg cgacttgaag    2220
gaaattcctg acaacatcaa gcaggatctt cagattaaac cggttaaatg gattgacgag    2280
gtcctgcaaa ttgcgctgca atacgcgccg gagcccttgc cggatgtggc cccggagatt    2340
gtcgcgaagg acgaaaaacg cgagtccgat tccaaggaaa gaattagcac gcat          2394
```

<210> SEQ ID NO 33
<211> LENGTH: 3726
<212> TYPE: DNA
<213> ORGANISM: Pseudomonas fluorescens

<400> SEQUENCE: 33

```
atggacgtag caggtaatgg cttcactgtg tcgcaacgca atcgcacccc ccgtttcaag      60
accacacccc tcacacccat agcactcggc ctggccttat ggctgggcca cggttccgtg     120
gccagggcag acgacaaccc ttacaccccg caggtactgg aatcggcgtt caggacagcc     180
gtcgcctcat tcggccctga gactgccgtg tacaaaaacc tcaggtttgc ctacgccgat     240
atcgtcgatc ttgcggccaa ggacttcgcg gcccagtccg gcaagttcga ttcggccctc     300
aagcaaaact atgagctgca acccgagaac ctgaccatcg cgccatgct cggcgacacc     360 cgtcggccac tggactacgc ctcgcgcctg gattactacc gcagccggct gttcagcaac     420
agcgcccgct acaccaccaa tatcctggac ttttccaagg ccattatcgc caacttgccg     480
gccgccaagc cttacaccta cgtagagcca ggcgttagca gcaacctcaa tgggcagttg     540
aacgccggcc agtcctgggc tggcgcaacc cgtgactgga cgccaacgc gcaaacctgg     600 aagaccccgg aagctcaggt caactctggc ctggaccgcc caacgcgta ctacgcctat     660 gccttgggca tcaccggtaa gggggtgaat gtcggcgtgc tggactcggg catcttcacc     720
gaacactccg agttccaggg caagaatgcc cagggccagg accgggtgca ggcggtgacc     780
tccacgggcg agtactacgc cacccatccg cgctaccgcc ttgaagtgcc cagtggtgag     840
ttcaagcagg gtgagcattt cagtatccca ggggaatacg acccggcgtt caacgacggg     900
catggcacgg agatgtccgg ggtgctggcc gccaaccgca acggcacggg tatgcacggc     960
attgccttcg acgccaacct gtttgtcgcc aacactggcg gcagcgacaa cgaccgctac    1020
caaggctcca cgacctcga ctacaacgca ttcatggcca gctacaacgc cctggcggcg    1080
aagaacgtgg cgatcgtcaa ccagagttgg gggcagagtt cgcgcgatga cgtggagaac    1140
cacttcggca acgtcggcga cagcgccgcg caaaaacctgc gcgacatgac cgccgcctat    1200
cgcccgttct gggacaaggc ccatgccggg cacaaaacct ggatgacgc catggccgat    1260 gcggcccggc aaaacacgtt catccagatc atctcggcgg gcaacgacag ccacggtgcc    1320
aacccggaca ccaattcgaa cctgccgttc ttcaaaccgg atatcgaagc taagttcctc    1380
tccatcactg gctacgacga aactagcgcc caggtctaca accgctgcgg tacgtccaag    1440
tggtggtgcg tgatgggcat atcggcgatt ccatctgccg gccccgaggg cgaaatcatc    1500
ccgaatgcca acggcacctc ggccgccgca ccgagcgttt ccggggcctt ggcgctagtg    1560
atgcaacgct tcccctacat gaccgccagc caggcgcggg acgtgttgct gaccacctcc    1620
agcctgcaag cgccggatgg cccggacacg ccggttggca cgctgaccgg tggccgcacc    1680
tacgacaacc tgcaaccggt gcatgatgcc gcgccgggtt tgccgcaagt gccgggtgtg    1740
gtcagtggct ggggcttgcc caacctgcaa aaagccatgc aagggccggg gcagttcctc    1800
```

```
ggtgcggtgg cagtggcgtt gcccagtggt acccgcgata tctgggccaa cccgatttcc    1860
gatgaagcca ttcgcgcccg ccgcgtagaa gacgctgccg aacaggctac ctgggccgcc    1920
accaagcagc aaaaaggctg gctcagtggc ctgcccgcca atgcctcggc cgacgatcag    1980
tttgaatacg acatcggtca tgcccgggag caggcaacac tcacccgcgg ccaggacgtg    2040
ctcaccggca gcacctacgt cggtagcctg gtcaagtccg gggatggcga gttggtgctg    2100
gaaggccaga cacctattc gggcagtact tgggtacgcg gaggcaaatt gtcggtggac     2160
ggcgcattga cctctgccgt gacggtagat agcagcgccg tgggcacgcg caatgccgat    2220
aacggcgtga tgaccacact gggcggcacc ctggccggca acggcacggt gggcgccttg    2280
accgtcaaca acggtgggcg agtggcccct gggcattcga taggcacact gcgcaccggc    2340
gatgtcacgt tcaacccggg ttcggtgtat gccgtcgaag tcggggccga tggccgcagc    2400
gaccagttgc agagcagcgg ggtggcgacc ctcaatggcg gtgtggtgag cgtgtcccta    2460
gagaacagcc ccaacctgtt gaccgccacc gaggcgcgca gcttgctggg ccagcagttc    2520
aatatcctca gcgccagcca aggtatccag gggcagtttg cagcgttcgc ccccaactac    2580
ctgttcattg gcactgcgct gaactatcaa ccgaaccagt tgaccctggc gatagcccgc    2640
aaccagacca ccttcgccag cgtcgcgcaa acccgcaatg agcggtcggt ggcgacggta    2700
gccgagacat tgggcgctgg cagcccggtc tacgaaagcc tgctggcgtc ggattccgct    2760
gcccaggcgc gggagggctt caaacaactt tcagggcaac tgcattcgga cgtggctgca    2820
gcgcaaatgg ctgacagccg ctacctgcgt gaagcggtca acgctcgcct gcaacaggcg    2880
caggcactgg actccagcgc gcagatcgac agccgtgaca acggcggctg ggtacagctg    2940
cttggtggac gcaacaacgt cagtggtgac aacaacgcca gcggctactc ctcgtccacc    3000
agcggcgtac tgctgggcct ggacaccgag gtgaacgacg gctggcgcgt gggcgcggcg    3060
accggttata cccaaagcca cctcaacggc cagtcggcgt cggcggacag cgacaactat    3120
cacctgtcgg tctatggcgg caaacgcttc gaggcgattg ccctgcgcct gggcggtgcc    3180
agcacctggc accgtctgga cacttcgcga cgggtggcct atgccaatca gtcggaccat    3240
gccaaggccg actacaacgc gcgtaccgac caagtgtttg ccgagatcgg ttacacccag    3300
tggaccgtgt ttgaacccct cgccaacctc acgtacctga actatcaaag cgactcgttc    3360
aaggaaaaag gcggtgccgc agccttgcat gccagccagc aaagccagga cgcgacactc    3420
tccaccctgg gcgtgcgtgg tcacactcag ttgccgctca cgtccacctc ggcggtgacc    3480
ctgcgcggtg agctgggttg ggagcaccag ttcggtgata ccgatcgtga agcttctctg    3540
aagtttgccg gtagtgacac ggccttcgcc gtaaacagcg tgcctgtggc cagggatggt    3600
gcggtgatca aagccagtgc ggagatggcc ttgaccaagg acacccttgt gtcgttgaac    3660
tacagtggct tgctctccaa ccgggtaac aacaacggga tcaatgccgg gtttaccttc    3720
ctgttc                                                              3726

<210> SEQ ID NO 34
<211> LENGTH: 1431
<212> TYPE: DNA
<213> ORGANISM: Pseudomonas fluorescens

<400> SEQUENCE: 34
atgtcaaaag taaagacaa agctattgta tctgccgcgc aagccagcac tgcttactcg      60
caaatcgata gcttcagcca tttgtatgac cgtggcggta acctcacagt caatggcaaa    120
ccgtcctaca ccgtggacca ggcagcgacc cagctgctgc gggatggtgc tgcgtaccgg    180
```

```
-continued gactttgatg gcaacggcaa gatcgatctg acctacacct tcctcacctc ggctacccag    240
agcaccatga acaaacatgg catctcgggg ttcagccagt tcaacaccca gcagaaagca    300
caggccgcac tggccatgca atcctgggcg gatgttgcca acgtgacctt taccgaaaag    360
gcttccggcg gtgacggcca catgacgttc ggtaactaca gcagtggcca ggacggcgcc    420
gcggccttcg cttacctgcc cggtaccggt gcaggctacg acggcacctc gtggtacctg    480
acaaacaaca gctacacgcc gaacaagacc ccggacctga acaactatgg ccggcagacc    540
ctgacccacg aaatcggcca caccctgggc ctggctcacc ctggcgacta caacgccggg    600
aacggcaacc cgacctataa cgacgcaacc tatggacagg acacgcgtgg ttatagcctc    660
atgagttact ggagcgagag caacaccaac cagaacttca gcaaaggcgg cgtcgaagct    720
tacgcttccg gcccgctgat cgacgacatt gccgcgatcc agaagctcta cggtgccaac    780
ctcagcaccc gcgccacgga caccacctac gggttcaact ccaacaccgg gcgtgatttc    840
ctcagcgcca cgtccaacgc cgacaagctg gtgttctcgg tatgggacgg tggcggcaac    900
gacaccctgg acttctccgg tttcacccag aaccagaaga tcaacctcac ggccacctcg    960
ttctctgatg tgggcggcct ggtgggcaac gtgtccatcg ccaagggcgt caccatcgag   1020
aacgcgttcg gcggcgcggg caacgacctg attattggta accaagttgc caacaccatc   1080
aagggcgggg ccggcaacga cctcatctac ggcggcggcg gtgcggacca actgtgggc    1140 ggcgcgggca gcgatacatt cgtgtacggt gccagttccg actccaagcc aggggctgcg   1200
gataagatct tcgacttcac gtccggttcg gacaagatcg acctgtctgg tatcaccaag   1260
ggtgcgggcg tgaccttcgt caacgccttt accgggcatg ccggcgatgc tgtactgagc   1320
tatgcctcgg gtaccaacct gggcaccttg gccgtggact tttccgggca cggcgtggcg   1380
gatttcctcg tcaccaccgt tggccaggcg gctgccagtg acatcgtagc c             1431
```